(12) United States Patent
Miller et al.

(10) Patent No.: US 7,034,054 B2
(45) Date of Patent: Apr. 25, 2006

(54) METHODS FOR THE PREVENTION AND TREATMENT OF CEREBRAL ISCHEMIA USING NON-ALPHA TOCOPHEROLS

(75) Inventors: Guy Miller, San Jose, CA (US); Lesley A. Brown, Reno, NV (US); Ughetta Del Balzo, San Jose, CA (US); Stephen Flaim, San Diego, CA (US); Sekhar Boddupalli, San Jose, CA (US); Bing Wang, Cupertino, CA (US)

(73) Assignee: Galileo Pharmaceuticals, Inc., Santa Clara, CA (US)

( * ) Notice: Subject to any disclaimer, the term of this patent is extended or adjusted under 35 U.S.C. 154(b) by 0 days.

(21) Appl. No.: 10/020,450

(22) Filed: Dec. 14, 2001

(65) Prior Publication Data

US 2002/0143049 A1 Oct. 3, 2002

Related U.S. Application Data

(60) Provisional application No. 60/256,269, filed on Dec. 15, 2000, and provisional application No. 60/196,580, filed on Jun. 6, 2001.

(51) Int. Cl.
*A61K 31/355* (2006.01)

(52) U.S. Cl. ...................................................... 514/458
(58) Field of Classification Search ................... 514/458
See application file for complete search history.

(56) References Cited

U.S. PATENT DOCUMENTS

| | | | |
|---|---|---|---|
| 3,755,560 A | 8/1973 | Dickert et al ................. 424/78 |
| 4,150,038 A | 4/1979 | Wingard ................... 260/345.2 |
| 4,254,105 A | 3/1981 | Fukuda ....................... 424/170 |
| 4,421,769 A | 12/1983 | Dixon et al. ................ 424/358 |
| 4,894,449 A | 1/1990 | Venero et al. .............. 536/118 |
| 4,960,764 A | 10/1990 | Figueroa, Jr. et al. ........ 514/63 |
| 4,977,282 A | 12/1990 | Baldwin et al. ............ 549/412 |
| 4,978,617 A | 12/1990 | Furuya ....................... 435/125 |
| 5,114,957 A | 5/1992 | Hendler et al. ............ 514/356 |
| 5,139,796 A | 8/1992 | Barkalow et al. ............. 426/3 |
| 5,200,214 A | 4/1993 | Barkalow et al. ............. 426/3 |
| 5,235,073 A | 8/1993 | Kim et al. .................. 549/408 |
| 5,296,469 A | 3/1994 | Orjales-Venero et al. ..... 514/27 |
| 5,504,220 A | 4/1996 | Kuo et al. .................. 549/408 |
| 5,606,080 A | 2/1997 | Ogata et al. ............... 549/408 |
| 5,648,331 A | 7/1997 | Koudsi et al. ................ 514/12 |
| 5,733,926 A | 3/1998 | Gorbach ..................... 514/456 |
| 5,756,538 A | 5/1998 | Cassels et al. ............. 514/456 |
| 5,801,159 A | 9/1998 | Miller et al. ................. 514/45 |
| 5,808,140 A | 9/1998 | Haridas ......................... 562/8 |
| 5,840,759 A | 11/1998 | Mitchell et al. ............ 514/610 |
| 5,855,892 A | 1/1999 | Potter et al. .............. 424/195.1 |
| 5,872,108 A | 2/1999 | Sandage, Jr. et al. ........ 514/49 |
| 5,914,112 A | 6/1999 | Bednar et al. ............ 424/144.1 |
| 5,945,432 A | 8/1999 | Bednar et al. .............. 514/301 |
| 5,952,374 A | 9/1999 | Clarkson, Jr. et al. ...... 514/456 |
| 6,048,891 A * | 4/2000 | Wechter ..................... 514/456 |
| 6,063,819 A | 5/2000 | Marangos et al. .......... 514/634 |
| 6,068,844 A | 5/2000 | Becker et al. ............ 424/184.1 |
| 6,083,982 A | 7/2000 | Wechter et al. ............. 514/529 |
| 6,150,402 A | 11/2000 | Wechter et al. ............. 514/458 |
| 6,242,479 B1 | 6/2001 | Wechter ..................... 514/456 |
| 6,297,281 B1 * | 10/2001 | Chabrier de Lassauniere et al. ........................... 514/589 |
| 6,346,544 B1 | 2/2002 | Hensley et al. ............. 514/458 |
| 6,410,589 B1 | 6/2002 | Wechter ..................... 514/458 |
| 6,555,575 B1 | 4/2003 | Wechter |
| 2002/0006954 A1 | 1/2002 | Hensley et al. ............. 514/458 |
| 2002/0165270 A1 | 11/2002 | Remacle et al. ............ 514/468 |
| 2004/0029954 A1 * | 2/2004 | Wechter ..................... 514/458 |
| 2004/0058986 A1 * | 3/2004 | Wechter ..................... 514/458 |
| 2004/0058987 A1 * | 3/2004 | Wechter ..................... 514/458 |

FOREIGN PATENT DOCUMENTS

| | | |
|---|---|---|
| EP | 0 326 987 | 9/1989 |
| JP | 58018374 | 2/1983 |
| WO | 98/09653 * | 3/1998 |
| WO | WO 00/35444 | 6/2000 |
| WO | WO 00/56348 A1 | 9/2000 |

OTHER PUBLICATIONS

Jiang et al., Proceedings of the National Academy of Sciences, 97/21, 11494–11499 (Oct. 10, 2000).*

Alberts, B. et al. (1994). *Molecular Biology of The Cell.* Garland Publishing, Inc., Third Edition. New York . pg. xiii–xxxviii. (Table of Contents).

Altura, B. M. and Gebrewold, A. (1996). "α–Tocopherol Attenuates Alcohol–Induced Cerebral Vascular Damage in Rats: Possible Role of Oxidants in Alcohol Brain Pathology ad Stroke," *Neuroscience Letters* 220:207–210.

Anderson, J. J. B. and Garner, S. C. (Dec. 1998). "Phytoestrogens and Bone," *Baillières Clin. Endocrinol. Metab.* 12(4):543–557.

Arora, A. et al. (1998). "Antioxidant Activities of Isoflavones and Their Biological Metobolites in a Liposomal System," *Arch. Biochem. Biophys.* 356(2):133–141.

Arthur, H. R. et al. (1956). "*An Examination of the Rutaceae of Hong Kong Part I. Flavonoid Glycosides from* Zanthoxylum *Species and the Occurrance of Optically Active Hesperetin,*" *J. Chem. Soc.* 127:632–635.

Atkinson, D. E. (1977). *Cellular Energy Metabolism and Its Regulation.* Academic Press, Inc., New York. pp. vii–viii. (Table of Contents).

Benet, L. Z. et al. (Dec. 1995). *Goodman and Gilman's The Pharmacological Basis of Therapeutics.* Ninth Edition, J.G., eta l. eds., McGraw–Hill Health Professions Division. pp. v–xii (Table of Contents).

(Continued)

*Primary Examiner*—Phyllis G. Spivack
(74) *Attorney, Agent, or Firm*—Carol A. Stratford; Michelle Y. Walker

(57) ABSTRACT

The present invention provides method for the treatment of a symptom of neuronal damage associated with cerebral ischemia comprising administering gamma-, beta-, or delta-tocopherol enriched tocopherol compositions.

43 Claims, 4 Drawing Sheets

OTHER PUBLICATIONS

Bernier, M. et al. (1991). "Pharmacological Studies of Arrhythmias Induced by Rose Bengal Photoactivation," *Free Radical Biology & Medicine* 10:287–296.

Bjeldanes, L. F. and Chang, G. W. (Aug. 1977). "Mutagenic Activity of Quercetin and Related Compounds," *Science* 197:577–578.

Boersma, B. J. et al. (Aug. 1999). "Chlorination and Nitration of Soy Isoflavones," *Arch. of Biochem. and Biophys.* 368(2):265–275.

Bonnefont–Rousselot, D. et al. (1999). "Antioxidant Effect of Probucol on $RO_2/O_2^-$ –Induced Peroxidation of Human Low–Density Lipoproteins," *Radiat. Res.* 151:343–353.

Bose, J. L. and Siddiqui, S. (1950). "A Note on the Constitution of Biochanin A," *J. Sci. Ind. Res. V.* 9B:25–26.

Brent, J. A. et al. (1993). "Role of Free Radicals in Toxic Hepatic Injury II. Are Free Radicals The Cause of Toxin–Induced Liver Injury?" *Clin. Toxicol.* 31(1):173–196.

Brown, J. P. et al. (1978). "Flavonoid Sweeteners. Synthesis and Intestinal Absorption of Selected Sulfoalkylated Hesperetin–3–$^{14}$C Derivative in the Rat," *J. Agric. Food Chem.* 26(6):1418–1422.

Cassio, D. et al. (Dec. 1991). "Hybrid Cell Lines Constitute A Potential Reservoir of Polarized Cells: Isolation and Study of Highly Differentiated Hepatoma–Derived Hybrid Cells Able to Form Functional Bile Canaliculi In Vitro," *J. Cell Biol.* 115(5):1397–1408.

Castro, L. et al. (Nov. 1994). "Aconitase Is Readily Inactivated by Peroxynitrite, but Not by Its Precursor, Nitric Oxide," *J. Biol. Chem.* 269(47):29409–29415.

Chen, M–F. et al. (1999). "The Role of Vitamin E on the Anti–Atherosclerotic Effect of Fish Oil in Diet–Induced Hypercholesterolemic Rabbits," *Prostaglandins and Other Lipid Mediat.* 57:99–111.

Choi, D.W. (Oct. 1988). "Glutamate Neurotoxicity and Diseases of the Nervous System," *Neuron* 1:623–634.

Ciolino, H. P. et al. (Jul. 1998). "Diosomin and Diosmetin Are Agonists of the Aryl Hydrocarbon Receptor That Differentially Affect Cytochrome P450 1A1 Activity," *Cancer Res.* 58:2754–2760.

Coward, L. et al. (1993). "Genistein, Daidzein, and Their β–Glycoside Conjugates: Antitumor Isoflavones in Soybean Foods from American and Asian Diets," *J. Agri. Food Chem.* 41:1961–1967.

Cuzzocrea, S. et al. (1998). "AntiInflammatory Effects of Mercaptoethylguanidine, A Combined Inhibitor of Nitric Oxide Synthase and Peroxynitrate Scavenger, in Carrageenan–Induced Models of Inflammation," *Free Radic. Biol. Med.* 24(3):450–459.

Danesh, J. et al. (May 1998). "Association of Fibrinogen, C–Reactive Protein, Albumin, or Leukocyte Count With Coronary Heart Disease: Meta–Analyses of Prospective Studies," *JAMA* 279(18):1477–1482.

DeGirolami, U. (Mar. 1982). "Neuropathology of Experimental Spinal Cord Ischemia in the Rabbit," *J. Neuropath. and Exp. Neurol.* 41(2):129–149.

Diplock, A. T. et al. (1998). "Functional Food Science and Defence Against Reactive Oxidative Species," *Br. J. Nutr.* 80(suppl. 1):S77–S112.

Dumon, M. F. et al. (1994). "Mise En Évidence De L' Effet Antilipoperoxydant Du 7 Rutinoside De La 3',5, 7–Trihydroxy–4'–Methoxy Flavone: Étude In Vitro," *Ann. Biol. Clin.* 52:265–270.

Esaki, S. et al. (1994). "Preparation and Taste of Certain Glycosides of Flavanones and of Dihydrochalcones," *Biosci. Biotechnol. Biochem* 58(8):1479–1485.

Fernholz, E. (Jun. 1937). "The Thermal Decomposition of α–Tocopherol," *Communication to The Editor* 59:1154–1155.

Fernholz, E. (Jun. 1937). "On the Constitution of α–Tocopherol," *Communication to the Editor* 60:700–705.

Flynn, C. J. et al. (1989). "Ischemia and Hypoxia" Chapter 40 In: *Basic Neurochemistry.* G. J. Siegel et al. eds., Raven Press, New York pp. 783–810.

Freneix–Clerc, M. et al. (1994). "In Vivo Study of the Antilipoperoxidant Effect of 3',5,7–Trihydroxy–4'–Methoxy Flavone 7 Rutinoside," *Ann. Biol. Clin.* 52:171–177. (English Summary).

Fridovich, I. (Jul. 1997). "Superoxide Anion Radical ($O_2^-$), Superoxide Dismutases, and Related Matters," *J. of Biol. Chem.* 272(30):18515–18517.

Fukuzawa, K. et al. (1982). "Antioxidant Activities of Tocopherols on $Fe^{2+}$– Ascorbate–Induced Lipid Peroxidation in Lecithin Liposomes," *Lipids* 17(7):511–513.

Ganguly, A. K. and Sarre, O. Z. (Feb. 1970). "Genistein and Daidzen, Metabolites of *Micromonospora Halophytica*," *Chemistry and Industry* 1:201.

Gebicki, S. and Gebicki J. M. et al. (1999). "Crosslinking of DNA and Proteins Induced by Protein Hydroperoxides," *Biochem. J.* 338:629–636.

Goldberg, M. P. and Choi, D. W. (1990). "Intracellular Free Calcium Increased in Cultured Cortical Neurons Deprived of Oxygen and Glucose," *Stroke* 21(suppl. III):III–75–III–77.

Gonzalez, M. J. (1990). "Serum Concentrations and Cellular Uptake of Vitamin E," *Med. Hypothesis.* 32:107–110.

Gores, G. J. et al. (1989a). "Intracellular pH During "Chemical Hypoxia" in Cultured Rat Hepatocytes: Protection by Intracellular Acidosis Against the Onset of Cell Death," *J. Clin. Invest.* 83:386–396.

Gores, G. J. et al. (1989b). "Swelling, Reductive Stress, and Cell Death During Chemical Hypoxia in Hepatocytes," *Am. J. Physiol.* 257(26):C347–C354.

Grau, A. and Ortiz, A. (1998). "Dissimilar Protection of Tocopherol Isomers Against Membrane Hydrolysis by Phospholipase $A_2$," *Chem. and Phys. Lipids* 91:109–118.

Grotta, J. C. et al. (Apr. 1988). "Efficacy and Mechanism of Action of a Calcium Channel Blocker After Global Cerebral Ischemia in Rats," *Stroke* 19(4):447–454.

Guidot, D. M. et al. (Aug. 1995). "Mitochondrial Respiration Scavenges Extramitochondrial Superoxide Anion Via a Nonenzymatic Mechanism," *J. Clin. Invest.* 96:1131–1136.

Guillot, R. et al. (1998). "Effect of Long–Term Treatment with a Purified Micronized Flavonoid Fraction on Pancreatic Mononuclear Cell Infiltration in Diabetic BB Rats," *Pancreas* 17(3):301–308.

Guoxian, S. et al. (Sep. 1980). "Studies on the Synthesis and Structure Biological Activity Relationships of Diadzein and its Derivatives," *Acta Pharmaceutica Sinica* 25(9):538–547.

Halliwell, B. (1997). "Antioxidants in Human Health and Disease," *Ann. Rev. Nutr.* 16:33–50.

Halliwell, B. et al. (1992). "Interaction of Nitrogen Dioxide with Human Plasma: Antioxidant Depletion and Oxidative Damage," *FEBS Lett.* 313(1):62–66.

Halliwell, B. (1995). "Oxygen Radicals, Nitric Oxide and Human Inflammatory Joint Disease," *Ann. of the Rheumat. Dist.* 54:505–510.

Halliwell, B. (Sep. 1994). "Free Radicals, Antioxidants, and Human Disease: Curiosity, Cause or Consequence?" *Lancet* 344:721–724.

Halliwell, B. et al. (1995). "The Characterization of Antioxidants," *Food Chem. Toxicol*. 33(7):601–617.

Hammons, G. J. et al. (1999). "Effects of Chemoprotective Agents on the Mebatolic Activation of the Carcinogenic Arylamines PhIP and 4–Aminobiphenyl in Human and Rat Liver Microsomes," *Nutr. and Cancer* 33(1):46–52.

Hara, H. et al. (1990). "Protective Effect of α–Tocopherol on Ischemic Neuronal Damage in the Gerbil Hippocampus," *Brain Research* 510:335–338.

Harman, D. et al. (Nov. 1998). "Towards Prolongation of the Healthy Life Span: Practical Approaches to Intervention$^{\alpha}$," *In Annals of the New York Academy of Sciences*. 854: total pp. 7. (Table of Contents).

Hawkins, R. D. et al. (1993). "Learning to Modulate Transmitter Release: Themes and Variations in Synatic Plasticity," *Annu. Rev. Neurosci*. 16:625–665.

Hochachka, P. W. et al. eds., (1993). *Surviving Hypoxia: Mechanisms of Control and Adaptation*. CRC Press. total pages 10. (Table of Contents).

Hodgson, J. M. et al. (1999). "Isoflavonoids Do Not Inhibit In Vivo Lipid Peroxidation in Subjects with High–Normal Blood Pressure," *Atherosclerosis* 145:167–172.

Honohan, T. et al. (1976). "Synthesis and Metabolic Fate of Hesperetin –3–$^{14}$C," *J. Agric. Food Chem*. 24(5):906–911.

Horowitz, R. M. (Oct. 1956). "Flavonoids of Citrus. I. Isolation of Diosmin from Lemons (*Citrus limon*)," *The J. of Org. Chem*. 21:1184–1185.

Hosny, M. and Rosazza, J. P. N. (1999). "Novel Isoflavone, Cinnamic Acid, and Triterpenoid Glycosides in Soybean Molasses," *J. Nat. Prod*. 62:853–858.

Ihrke, G. et al. (1993). "WIF–B Cells. An In Vitro Model for Studies of Hepatocyte Polarity," *J. Cell Biol*. 123:1761–1775.

Infante, J. P. (1986). "Vitamin E and Selenium Participation in Fatty Acid Desaturation A Proposal for an Enzymatic Function of These Nutrients," *Mol. and Cell. Biochem*. 69:93–108.

Infante, J. P. and Huszagh, V. A. (1998). "Analysis of the Putative Role of 24–Carbon Polyunsaturated Fatty Acids in the Biosynthesis of Docosapentaenoic (22:5n–6) and Docosahexaenoic (22:6n–3) Acids," *FEBS Lett*. 431:1–6.

Infante, J. P. (1999). "A Function for the Vitamin E Metabolite α–Tocopherol Quinone as an Essential Enzyme Cofactor for the Mitochondrial Fatty Acid Desaturases," *FEBS Lett*. 446:1–5.

Ischiropoulos, H. et al. (Nov. 1992). "Peroxynitrite Formation From Macrophage–Derived Nitric Oxide," *Arch. of Biochem .and Biophys*. 298(2):446–451.

Jacobs, T. P. (1987). "Deteriorating Stroke Model: Histopathology, Edema, and Eicosanoid Changes Following Spinal Cord Ischemia in Rabbits," *Stroke* 18(4):741–750.

Jacobs, T. P. et al. (1992). "Blood Flow and Vascular Permeability During Motor Dysfunction in a Rabbit Model of Spinal Cord Ischemia," *Stroke* 23(3):367–373.

Jenkinson, S. G. (1989). "Free Radical Effects on Lung Metabolism," *Clin. Chest Med*. 10(1):37–47.

Jiang, Q. et al. (Oct. 2000). "γ–Tocopherol and its Major Metabolite, In Contrast to α–Tocopherol, Inhibit Cyclooxygenase Activity in Macrophages and Epithelial Cells," *PNAS* 97(21):11494–11499.

Joannou, G. E. et al. (1995). "A Urinary Profile Study of Dietary Phytoestrogens. The Identification and Mode of Metabolism of New Isoflavonoids," *J. Steroid Biochem. Mol. Biol*. 54(3/4):167–184.

Kanno, T. et al. (1996). "Inhibition of Neutrophil–Superoxide Generation by α–Tocopherol and Coenzyme Q", *Free Radic. Res*. 24(4):281–289.

Kavutcu, M. and Melzig, M. F. (1999). "In Vitro Effects of Selected Flavonoids on the 5'–Nucleotidase Activity," *Pharmazie* 54:457–459.

Keung, W–M. (Nov./Dec. 1993). "Biochemical Studies of a New Class of Alcohol Dehydrogenase Inhibitors from *Radix puerariae*," *Alcohol. Clin. and Exp. Res*. 17(6):1254–1260.

King, R. A. (1998). "Daidzein Conjugates are more Bioavailable Than Genistein Conjugates in Rats," *Am. J. Cli. Nutr*. 68(Suppl):1496S–1499S.

Kinouchi, H. et al. (Dec. 1991). "Attenuation of Focal Cerebral Ischemic Injury in Transgenic Mice Overexpressing CuZn Superoxide Dismutase," *Proc. Natl. Acad. Sci. USA* 88:11158–11162.

Ko, H–Y. and Park–Ko, I. (Aug. 1999). "Electrophysiologic Recovery After Vitamin E–Deficient Neuropathy," *Arch. Phys. Med. Rehabil*. 80:964–967.

Kojiima, S. et al. (Jan. 1990). "Prognosis and Disability of Stroke Patients After 5 Years in Akita, Japan," *Stroke* 21:72–77.

Kowaltowski, A. J. et al. (1995). "$CA^{2+}$–Induced Mitochondrial Membrane Permeabilization: Role of Coenzyme Q Redox State ," *Am. J. Physiol*. 269(*Cell Physiol*. 38): C141–C147.

Kowaltowski, A. J. et al. (1996). "Effect of Inorganic Phosphate Concentration of the Nature of Inner Mitochondrial Membrane Alterations Mediated by $CA^{2+}$ Ions," *J. Biol. Chem*. 271(6):2929–2934.

Kowaltowski, A. J. et al. (1998). "Activation of the Potato Plant Uncoupling Mitochondrial Protein Inhibits Reactive Oxygen Species Generation by the Respiratory Chain," *FEBS Letters* 425:213–216.

Kubo, K. et al. (1997). "Changes in Susceptibility of Tissues to Lipid Peroxidation After Ingestion of Various Levels of Docosahexaenoic Acid and Vitamin E," *Br. J. Nutr*. 78:655–669.

Kuppusamy, U. R. and Daz, N. P. (1993). "Antilipolytic Action of Hesperetin in Rat Adipocytes," *Planta Med*. 59:508–512.

Langley, S. C. et al. (1992). "Dietary Supplementation of Vitamin E Fails to Prevent the Development of Hyperoxic Lung Injury in the Premature Guinea Pig," *Comp. Biochem. Physiol*. 103A(4):793–799.

Lapĉík, O. et al. (1997). "A Novel Radioimmunoassay For Diadzein," *Steroids* 62:315–320.

LeBel, C. P. et al. (1992). "Evaluation of the Probe 2',7'–Dichlorofluorescin as an Indicator of Reactive Oxygen Species Formation and Oxidative Stress," *Chem. Res. Toxicol*. 5:227–231.

Lecanu, L. et al. (Feb. 1998)."Deleterious CA–Independent NOS Activity After Oxidative Stress in Rat Striatum ," *Neuroreport* 9(3):559–563.

Leth, T. and Søndergaard, H. (1977). "Biological Activity of Vitamin E Compounds and Natural Materials by the Resorption–Gestation Test, and Chemical Determination of the Vitamin E Activity in Foods and Feeds," *J. Nutr*. 107:2236–2243.

Lyn–Cook, B. D. et al. (1999). "The Effects of Phytoestrogens on Human Pancreatic Tumor Cells In Vitro," *Cancer Lett*. 142:111–119.

MacManus, J. P. et al. (1993). "Global Ischemia Can Cause DNA Fragmentation Indicative of Apoptosis in Rat Brain," *Neurosci. Lett*. 164:89–92.

Markham, K. R. and Bloor, S. J. (1998). "Analysis and Identification of Flavonoids in Practice," *Flavonoids in Health and Disease*. Rice–Evans and Packer. eds., Marcel Dekker, Inc.

Matsugo, S. et al. (1997). "The Lipoic Acid Analogue 1,2–Diselenolane–3–Pentanoic Acid Protects Human Low Density Lipoprotein Against Oxidative Modification Mediated by Copper Ion," *Biochem. Biophys. Res. Comm.* 240:819–824.

Mazzoni, M. R. et al. (Jul. 1991). "Structural Analysis of Rod GTP–Binding Protein, $G_t$: Limited Proteolytic Digestion Pattern of $G_t$, with Four Proteases Defines Monoclonal Antibody Epitope," *J. of Biol. Chem*. 266(21):14072–14081.

Melzig, M. F. and Loose, R. (1999). "Inhibition of Lipopolysaccharide (LPS)–Induced Endothelial Cytotoxicity by Diosmin," *Pharmazie* 54:298–299.

Merdes, A. et al. (Oct. 1991). "Filensin: A New Vimentin–Binding, Polymerization–Competent, and Membrane–Associated Proteins of the Lens Fiber Cell," *J. Cell Biol*. 115(2):397–410.

Mezei, M. et al. (1982). "Liposomes–A Selective Drug Delivery System for the Topical Route of Administration: Gel Dosage Form," *J. Pharm. Pharmacol*. 34:473–474.

Mezei, M. et al. (Sep. 1985). *Topics in Pharmaceutical Sciences 1985*. D. D. Breimer and P. Speiser eds., Elsevier Science Publishers, pp. 345–358.

Molinari, G. F. (1986) "Experimental Models of Ischemic Stroke," Chapter 5 In *Stroke: Pathophysiology, Diagnosis and Management*. H. J. M. Barnett et al. (eds.), Churchill Livingstone, New York. pp. 57–73.

Neuzil, J. and Baoutina, A. (1998). "α–Tocoherol in Atherogenesis: Do We Know its Real Role?," *Card. Drugs. and Ther*. 12:421–423.

Ng, H. P. et al. (1999). "Toxicological and Antioxidant Effects of Short–Term Dehydroepiandrostererone Injection in Young Rats Fed Diets Deficient or Adequate in Vitamin E," *Food and Chem. Toxicol*. 37:503–508.

Obata, T. (Jan. 1997). "Use of Microdialysis for In–Vivo Monitoring of Hydroxyl Free–Radical Generation in the Rat," *J. Pharm. Pharmacol*. 49:724–730.

Park, L. C. H. et al. (2000). "Metobolic Impairment Elicits Brain Cell Type–Selective Changes in Oxidative Stress and Cell Death in Culture," *J. Neurochem*. 74:114–124.

Pope, G. S. and Elcoate, P. V. (Oct. 1953). "Isolation of an Oestrogenic Isoflavone (Biochanin A) From Red Clover," *Chemistry and Industry*. p. 1092.

Pryor, W. A. and Squadrito, G. L. (1995). "The Chemistry of Peroxynitrite: A Product from the Reaction of Nitric Oxide with Superoxide," *Am. J. Physiol*. 268:L699–L722.

Radi, R. et al. (Mar. 1991). "Peroxynitrite Oxidation of Sulfhydryls: The Cytotoxic Potential of Superoxide and Nitric Oxide," *J. of Biol. Chem*. 266(7):4244–4250.

Reiter, R. J. et al. (1998). "Reactive Oxygen Intermediates, Molecular Damage, and Aging: Relation to Melatonin," *Ann. N.Y. Acad. Sci*. 854:410–424.

Ricciarelli, R. et al. (1998). "α–Tocoherol Specifically Inactivates Cellular Protein Kinase Cα by Changing its Phosphorylation State," *Biochem. J*. 334:243–249.

Ridker, P. M. (1999). "Hormone Replacement Therapy and Increased Plasma Concentration of C–Reactive Protein," *Circulation* 100(7):713–716.

Ridker, P.M. (Mar. 2000). "C–Reactive Protein and Other Markers of Inflammation in the Prediction of Cardiovascular Disease in Women," *N. Engl. J. of Med*. 342(12):836–843.

Rizzo, A. F. et al. (1994). "Protective Effect of Antioxidants Against Free Radical–Mediated Lipid Peroxidation Induced by DON or T–2 Toxin," *J. Vet. Med. A*. 41:81–90.

Robertson, C. S. et al. (Apr. 1986). "Protection Against Experimental Ischemic Spinal Cord Injury," *J. Neurosurg*. 64:633–642.

Rowland, M. and Tozer, T. N. (1995). *Clinical Pharmacokinetics:Concepts and Applications*. Third edition, Williams & Wilkins, p. ix–x. (Table of Contents).

Saini, T. et al. (Sep. 1998). "Protective Ability of Acetylsalicylic Acid (Aspirin) to Scavenge Radiation Induced Free Radicals in J774A.1 Macrophage Cells," *Res. Comm. in Mol. Pathol. and Pharmacol*. 101(3):259–268.

Saija, A. et al. (1995). "Flavonoids as Antioxidant Agents: Importance of Their Interaction with Biomembranes," *Free Radic. Biol. and Med*. 19(4):481–486.

Salvemini, D. et al. (1996). "Nitric Oxide: A Key Mediator in the Early and Late Phase of Carregeenan–Induced Rat Paw Inflammation," *Br. J. Pharmacol*. 118:829–838.

Salvemini, D. et al. (1996). "Evidence of Peroxynitrite Involvement in the Carrageenan–Induced Rat Paw Edema," *Eur. J. Pharmacol*. 303:217–220.

Sanders, R. (Apr. 1997). "UC Berkeley and Australian Researchers Call into Question Current Formulation of Vitamin E Supplements," News Release <http:www.berkeley.edu/news/media/releases/97legacy/christen.html> (visited on Feb. 26, 2002). total pp. 3.

Sargeant, P. et al. (Aug. 1993). "ADP–and Thapsigargin–Evoked $Ca^{2+}$ Entry and Protein–Tyrosine Phosphorylation Are Inhibited by the Tyrosine Kinase Inhibitors Genistein and Methyl–2, 5–Dihydroxycinnamate in Fura–2–Loaded Human Platelets," *J. Biol. Chem*. 268(24):18151–18156.

Sathyamoorthy, N. et al. (Feb. 1994). "Stimulation of pS2 Expression by Diet–Derived Compounds," *Cancer Res*. 54:957–961.

Scambia, G. et al. (1990). "Synergistic Antiproliferative Activity of Quercetin and Cisplatin on Ovarian Cancer Cell Growth," *Anti–Cancer Drugs* 1:45–48.

Schwartz, G. G. et al. (1996). "Low–Dose Inotropic Stimulation During Left Ventricular Ischaemia Does not Worsen Post–Ischaemic Dysfunction," *Cardiovasc. Res*. 32:1024–1037.

Shahidi, F. and Wanasundara, P. D. (1992). "Phenolic Antioxidants," *Crit. Rev. in Food Sci. Nutri*. 32(1):67–103.

Shanks, M. R. et al. (1994). "An Improved Polarized Rat Hepatoma Hybrid Cell Line: Generation and Comparison with its Hepatoma Relatives and Hepatocytes In Vivo," *J. of Cell Science* 107:813–825.

Siesjo, B. K. (1981). "Cell Damage in the Brain: A Speculative Synthesis," *J. Cereb. Blood Flow Metab*. 1:155–185.

Smit, G. et al. (Jan. 1992). "*Bradyrhizobium japonicum* $NodD_1$ Can Be Specifically Induced by Soybean Flavonoids That Do Not Induce the NodYABCSUIJ Operon," *J. of Biol. Chem*. 267(1):310–318.

Strohschein, S. et al. (1998). "Shape Selectivity of $C_{30}$ Phases for RP–HPLC Separation of Tocopherol Isomers and Correlation with MAS NMR Data from Suspended Stationary Phases," *Anal. Chem*. 70(1):13–18.

Suzuki, H. et al. (1998). "Increase in Intracellular Hydrogen Peroxide and Upregulation of a Nuclear Respiratory Gene Evoked by Impairment of Mitochondrial Electron Transfer in Human Cells," *Biochem. and Biophys. Res. Commun.* 249(2):542–545.

Szabo, C. et al. (1997). "Endothelial Dysfunction in a Rat Model of Endotoxic Shock: Importance of the Activation of Poly (ADP–Ribose) Synthetase by Peroxynitride," *J. of Clin. Invest.* 100(3):723–735.

Teel, R. W. and Huynh, H. (1998). "Modulation by Phytochemicals of Cytochrome P450–Linked Enzyme Activity," *Cancer Lett.* 133:135–141.

Thabrew, M. I. et al. (1999). "Effect of Oral Supplementation with Vitamin E on the Oxido–Reductive Status of Red Blood Cells in Normal Mice and Mice Subject to Oxidative Stress by Chronic Administration of Adriamycin," *Ann. Clin. Biochem.* 36:216–220.

Toda, S. and Shirataki, Y. (1999). "Short Communication: Inhibitory Effects of Isoflavones on Lipid Peroxidation by Reactive Oxygen Species," *Phytother. Res.* 13:163–165.

Traber, M. G. and Packer, L. (1995). "Vitamin E: Beyond Antioxidant Function," *Am. J. Clin. Nutr.* 62(suppl):1501S–1509S.

Unruh, H. W. (Feb. 1995). "Lung Preservation and Lung Injury," *Chest Surg. Clin. of North Am.* 5(1):91–106.

Wagner, J. G. (1993). *Pharmacokinetics for the Pharmaceutical Scientist*. Technomi.c Publishing Co. Inc., Lancaster, PA. p. v–xi. (Table of Contents).

Watabe, S. et al. (1997). "SP–22 is a Thioredoxin–Dependent Peroxide Reductase in Mitochondria," *Eur. J. Biochem.* 249:52–60.

Watson, B. D. and Ginsberg, M. D. (1989). "Ischemic Injury in the Brain: Role of Oxygen Radical–Mediated Processes," *In Annals of the New York Academy of Sciences: Archidonic Acid Metabolism in the Nervous System*. Amiram I. Barkai and Nicolas G. Bazan eds., 559:269–281.

Wechter, W. J. et al. (Jun. 1996). "A New Endogenous Natriuretic Factor: LLU–α," *Proc. Natl. Acad. Sci. USA* 93:6002–6007.

Wizemann, T. M. et al. (Dec. 1994). "Production of Nitric Oxide and Peroxynitrite in the Lung During Acute Endotoxemia," *J. Leukoc. Biol.* 56:759–768.

Wong, E. (May 1962). Detection and Estimation of Oestrogenic Constituents in Red Clover *J. Sci Food Agr.* 13:304–308.

Yamamoto, M. et al. (Nov./Dec. 1983). "A Possible Role of Lipid Peroxidation in Cellular Damages Caused By Cerebral Ischemia and the Protective Effect of α–Tocopherol Administration," *Stroke* 14(6):977–982.

Yin, F. et al. (1999). "Growth Inhibitory Effects of Flavonoids in Human Thyroid Cancer Cell Lines," *Thyroid* 9(4):369–376.

Zhao, W. et al. (1996). "Neuroprotective Effects of Hypothermia and U–78517F in Cerebral Ischemia Are Due to Reducing Oxygen–Based Free Radicals: An Electron Paramagnetic Resonance Study With Gerbils," *J. of Neurosci. Res.* 45:282–288.

Zhou, J. R. et al. (1999). "Soybean Phytochemicals Inhibit the Growth of Transplantable Human Prostate Carcinoma and Tumor Angiogenesis in Mice," *J. Nutr.* 129:1628–1635.

Zivin, J. A. and DeGirolami, U. (Mar. and Apr. 1980). "Spinal Cord Infarction: A Highly Reproducible Stroke Model," *Stroke* 11(2):200–202.

Fryer, M.J. (1998). "Vitamin E Status and Neurodegenerative Disease." *Nutritional Neuroscience* 1(5):327–351.

Saldeen, et al. (1999). "Differential Effects of α– and γ–Tocopherol on Low–Density Lipoprotein Oxidation, Superoxide Activity, Platelet Aggregation & Arterial Thrombogenesis." *Journal of the American College of Cardiology* 34(4):1208–1215.

Christen, S. et al. (1997). γ–Tocopherol Traps Mutagenic Electrophiles such as NOx and Complements α–Tocopherol: Physiological Implications. *Proc. Natl. Acad. Sci.* 94:3217–3222.

Paranich, et al. (1991). "Age–related Tocopherol Content of Normal and Ischemic Heart and Liver of Rats." *Fiziol. Zh. (Kiev)* 37(5):16–19. (Abstract only).

Cooney, et al. (1993). "γ–Tocopherol detoxification of nitrogen dioxide: Superiority to α–tocopherol." *Proc. Natl. Acad. Sci. USA*. 90:1771–1775.

Copin, J. et al. 1998. Trolox and 6,7–dinitroquinoxaline–2, 3–dione prevents necrosis but not apoptosis in cultured neurons subjected to oxygen deprivation. *Brain Research* 784:25–36.

Kobayashi et al., Free Radical Research (2000), 32(2), 115–125.*

The Merck Manual, Seventeenth Edition (1999), 1417–1424.

* cited by examiner

VOLUMETRIC COMPARISON
OF TOTAL INFARCT
Gamma-Tocopherol and Gamma-CEHC
at MCAO

VOLUMETRIC COMPARISON
OF TOTAL INFARCT
Gamma-Tocopherol and Gamma-CEHC
at Reperfusion

Figure 3

Formula 1

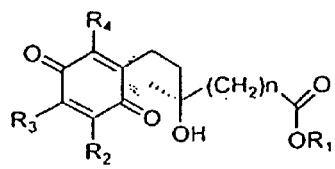

R1 = H or CH3 or glucuronide
R2 = H or CH3
R3 = H or CH3
R4 = H or CH3
n  = 2 or 4

Formula 2

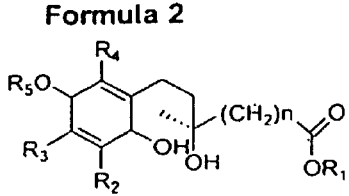

R1 = H or CH3 or glucuronide
R2 = H or CH3
R3 = H or CH3
R4 = H or CH3
R5 = H or CH3 or glucuronide or acetate or succinate
n  = 2 or 4

Formula 3

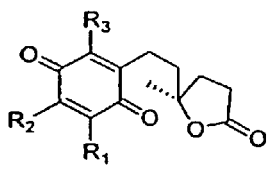

R1 = H or CH3
R2 = H or CH3
R3 = H or CH3

Formula 4

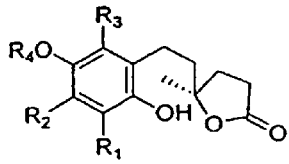

R1 = H or CH3
R2 = H or CH3
R3 = H or CH3
R4 = H or CH3 or glucuronide or acetate or succinate

Formula 5

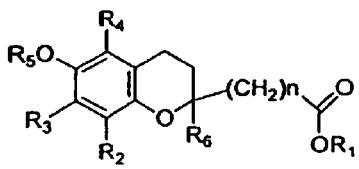

R1 = H or CH3 or glucuronide
R2 = H or CH3
R3 = H or CH3
R4 = H or CH3
R5 = H or CH3 or glucoronide or acetate or succinate
R6 = CH3 with S and/or R configuration
n  = 2 or 4

METHODS FOR THE PREVENTION AND TREATMENT OF CEREBRAL ISCHEMIA USING NON-ALPHA TOCOPHEROLS

CROSS-REFERENCE TO RELATED APPLICATIONS

This application claims the benefit of U.S. Provisional Application Serial No. 60/256,269 filed Dec. 15, 2000; and U.S. Provisional No. 60/296,580, filed Jun. 6, 2001 all hereby incorporated herein in their entirety.

TECHNICAL FIELD

This invention generally relates to compositions and methods comprising gamma-tocopherol and/or a metabolite and/or a derivative thereof; beta-tocopherol and/or a metabolite and/or a derivative thereof; and delta-tocopherol and/or a metabolite and/or derivative thereof, for preventing or treating cerebral ischemia in a mammalian subject. The invention also relates to methods of making such compositions.

BACKGROUND ART

Ischemia may be defined as the loss of blood flow to a tissue. Cerebral ischemia, also known as stroke, is the interruption or reduction of blood flow in the arteries feeding the brain. Loss of blood flow to a particular vascular region is known as focal ischemia; loss of blood flow to the entire brain, global ischemia. When deprived of blood, and thus, oxygen and glucose, brain tissue may undergo ischemic necrosis or infarction. The metabolic events thought to underlie such cell degeneration and death include: energy failure through ATP depletion; cellular acidosis; glutamate release; calcium ion influx; stimulation of membrane phospholipid degradation and subsequent free-fatty-acid accumulation; and free radical generation. Examples of methods for the treatment of stroke have been described in U.S. Pat. Nos. 5,872,108; 5,914,112; 5,945,432; 6,063,819 and 6,068,844.

Vitamin E (alpha-tocopherol) and closely related compounds have long been thought to act as antioxidants. Halliwell (1996) *Ann. Rev. Nutr*. 16:33–50; Diplock et al. (1998) *Br. J. Nutr*. 80: S77–112. Alpha-tocopherol can prevent peroxidation in vitro, and this function can be replaced by other antioxidants. However, additional functions for vitamin E seem likely, since other antioxidants cannot relieve all the symptoms of vitamin E deficiency. There is increasing evidence that tocopherols are involved in the control of cell proliferation and differentiation. Traber et al. (1995) *Am. J Clin. Nutr*. 62: 1501S–1509S. Alpha-tocopherol also functions as a scavenger of active nitrogen species (Halliwell et al. (1992) *FEBS Lett*. 313:62–66) and a gamma-tocopherol metabolite is an alleged natriuretic (Wechter et al. (1996) *Proc. Natl. Acad. Sci. USA* 93:6002–6007). See also U.S. Pat. Nos. 6,150,402; 6,083, 982; 6,048,891, and 6,242,479 specifically incorporated herein in their entirety. Alpha-tocopherol has been alleged to have an effect on cerebral ischemia. Yamamoto et al., 1983, *Stroke*, vol. 14:977–982; Hara et al., 1990, *Brain Research*, vol. 510: 335–338; and Altura, et al., 1996, *Neuroscience Letters*, vol. 220:207–210. In addition, alpha-tocopherol or its quinone derivatives may be involved in fatty acid desaturation. Infante (1986) *Mol. Cell. Biochem*. 69:93–108; Infante et al. (1998) *FEBS Lett*. 431:1–6. An additional major role of dietary alpha-tocopherol may be as a precursor of its D-alpha-tocopherolquinone metabolite whose semiquinone radical is required as an essential enzyme cofactor by carnitine-dependent, channeled mitochondrial fatty acid desaturases. Infante (1999) *FEBS Lett*. 446:1–5.

Tocopherols, while generally similar in overall chemical structure, may vary in biological function. Alpha-tocopherol is generally considered the most biologically active form of vitamin E; it is also the most abundant in adult human serum. Neuzil et al. (1998) *Card. Drugs. Ther*. 12:421–423; Strohschein et al. (1998) *Anal. Chem*. 70:13–18; Gonzalez (1990) *Med. Hypothes*. 32:107–110. Alpha-tocopherol has a greater antioxidant activity than the other tocopherols. Fukuzawa et al. (1982) *Lipids* 17:511–13. Alpha-tocopherol, but not beta-tocopherol, inhibits protein kinase C function. Ricciarelli et al. (1998) *Biochem. J*. 334:243–249. However, both alpha- and beta-tocopherol inhibit porcine pancreatic phospholipase A2 activity. Grau et al. (1998) *Chem. Phys. Lipids* 91:109–118. Alpha-, beta-, gamma- and delta-tocopherol were all able to inhibit superoxide generation by neutrophils. Kanno et al. (1996) *Free Radic. Res*. 24:181–189. Delta-tocopherol has only one hundredth of the activity of natural alpha-tocopherol in the Evans resorption sterility test for vitamin E.

In the treatment of cerebral ischemia, free radical scavengers/antioxidants have been used to improve cerebral blood flow and/or neurological outcome. In general, the effects of these compounds on infarct volume have been inconsistent. U.S. Pat. No. 5,872,108. For example, superoxide dismutase inhibitors have been found to reduce infarct volume only when injected intracerebroventricularly. See, Kinouchi et al. (1991) *Proc. Natl. Acad. Sci. USA* 88:11158–11162. Other compounds, such as lubeluzole, have been shown to have clinical benefit for cerebral ischemia but with a very narrow margin of safety. Diener et al. (1995) *Stroke* 26:30.

Cerebral ischemia is one of the major causes of human neurological morbidity and mortality with poor prognosis associated with stroke recovery. Thus, a need remains for identification of effective compositions and methods which aid in the survival and recovery of cells during injury associated with cerebral ischemia or for mammalian subjects at risk for injury associated with cerebral ischemia.

The disclosure of all patents and publications cited herein are incorporated by reference in their entirety.

DISCLOSURE OF THE INVENTION

The present invention relates to compositions and methods for the treatment and prevention of cerebral ischemia in a mammalian subject. Accordingly, the present invention provides methods for treating and/or ameliorating the symptoms of a cerebral ischemic condition in a mammalian subject, comprising administering to the subject an effective amount of a non-alpha tocopherol enriched tocopherol composition, and by said administering, reducing neuronal damage related to said cerebral ischemic condition. In some embodiments, the non-alpha tocopherol enriched tocopherol composition is a gamma-tocopherol enriched tocopherol composition. In other embodiments, the non-alpha tocopherol enriched tocopherol composition is a gamma-tocopherol metabolite enriched composition. In additional embodiments, the non-alpha tocopherol enriched tocopherol composition is a beta-tocopherol enriched tocopherol composition. In further embodiments, the non-alpha tocopherol enriched tocopherol composition is a beta-tocopherol metabolite enriched composition. In yet other embodiments, the non-alpha tocopherol enriched tocopherol composition is a delta-tocopherol enriched tocopherol composition. In other embodiments, the non-alpha tocopherol enriched tocopherol composition is a delta-tocopherol metabolite enriched composition.

In some embodiments of the present invention, the cerebral ischemic condition is secondary to an occlusion of the cerebral vasculature and in other embodiments, the occlusion is due to a thromboembolis. In further embodiments, the cerebral ischemia is due to a spasm of the coronary vasculature. In additional embodiments, the cerebral ischemic condition is secondary to a cessation of cardiac function. In further embodiments, the cerebral ischemic condition is secondary to a cardiopulmonary bypass procedure. In yet additional embodiments, the cerebral ischemic condition is secondary to a hemorrhagic event in the cerebral vasculature.

In some aspects of the present invention, a gamma tocopherol enriched tocopherol composition comprises at least 50%, at least 55%, at least 60%, at least 65%, at least 70%, at least 75%, at least 80%, at least 85%, at least 90%, at least 95%, or at least 98% gamma-tocopherol. In other aspects, a beta-tocopherol enriched tocopherol composition comprises at least 50%, at least 55%, at least 60%, at least 65%, at least 70%, at least 75%, at least 80%, at least 85%, at least 90%, at least 95%, or at least 98% beta-tocopherol. In yet other aspects, a delta-tocopherol enriched tocopherol composition comprises at least 50%, at least 55%, at least 60%, at least 65%, at least 70%, at least 75%, at least 80%, at least 85%, at least 90%, at least 95%, or at least 98% delta-tocopherol. In further aspects, a gamma tocopherol metabolite enriched composition comprises at least 50%, at least 55%, at least 60%, at least 65%, at least 70%, at least 75%, at least 80%, at least 85%, at least 90%, at least 95%, or at least 98% gamma-tocopherol metabolite. In some embodiments, the gamma-tocopherol metabolite is gamma-CEHC. In other aspects, a beta-tocopherol metabolite enriched composition comprises at least 50%, at least 55%, at least 60%, at least 65%, at least 70%, at least 75%, at least 80%, at least 85%, at least 90%, at least 95%, or at least 98% beta-tocopherol metabolite. In yet other aspects, a delta-tocopherol metabolite enriched composition comprises at least 50%, at least 55%, at least 60%, at least 65%, at least 70%, at least 75%, at least 80%, at least 85%, at least 90%, at least 95%, or at least 98% delta-tocopherol metabolite.

In some embodiments of the present invention, a composition comprises a non-alpha tocopherol in a range of 1–1000 mg per kg body weight of said mammalian subject. In yet other embodiments, a composition comprises a non-alpha tocopherol in a range of 1–50 mg per kg body weight of said mammalian subject. In further embodiments, a composition comprises a non-alpha tocopherol in a range of 10–100 mg per kg body weight of said mammalian subject.

The present invention also encompasses novel compositions and methods for making such compositions. In some embodiments of the present invention, a composition is a nutritional composition. In other embodiments, a composition is a pharmaceutical composition. In some embodiments, the administering is via an enteral route. In other embodiments, the administering is via an oral route. In yet further embodiments, the administering is via a parenteral route.

In other aspects the present invention provides gamma-tocopherol enriched tocopherol compositions comprising gamma tocopherol in an amount effective to reduce neuronal damage related to a cerebral ischemic condition. In further embodiments, the present invention provides beta-tocopherol enriched tocopherol compositions comprising beta tocopherol in an amount effective to reduce neuronal damage related to a cerebral ischemic condition. In further embodiments, the present invention provides delta-tocopherol enriched tocopherol compositions comprising delta tocopherol in an amount effective to reduce neuronal damage related to a cerebral ischemic condition.

The other aspects the present invention provides gamma-tocopherol metabolite or derivative enriched compositions comprising a gamma tocopherol metabolite or derivative in an amount effective to reduce neuronal damage related to a cerebral ischemic condition. In preferred embodiments, the gamma-tocopherol metabolite is gamma-CEHC. In further embodiments, the present invention provides beta-tocopherol metabolite or derivative enriched compositions comprising a beta tocopherol metabolite or derivative in an amount effective to reduce neuronal damage related to a cerebral ischemic condition. In further embodiments, the present invention provides delta-tocopherol metabolite or derivative enriched compositions comprising a delta tocopherol metabolite or derivative in an amount effective to reduce neuronal damage related to a cerebral ischemic condition.

BRIEF DESCRIPTION OF THE DRAWINGS

FIG. 3 illustrates 5 general formulas of tocopherol metabolites.

MODES FOR CARRYING OUT THE INVENTION

Figure 1:
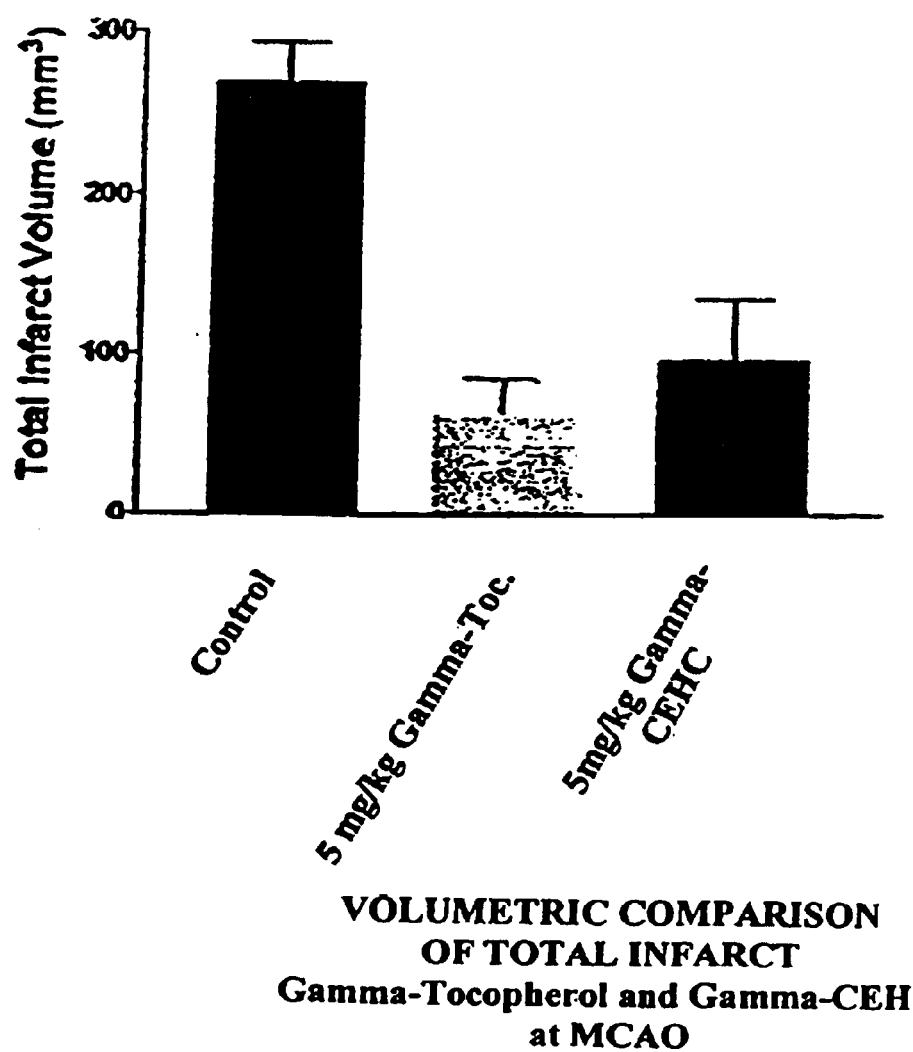
FIG. 1 shows the effect of gamma-tocopherol and its metabolite, gamma-carboxy ethyl hydroxy chroman (gamma-CEHC), on the volumetric comparison of total infarct with administration of gamma-tocopherol and gamma-CEHC at the time of Middle Cerebral Artery Occlusion (MCAO) as described in Example 2.

The present invention generally relates to naturally-occurring compounds as well as synthetic derivatives of naturally occurring compounds and non-naturally occurring mixtures of naturally-occurring compounds that can be used in nutritional and pharmaceutical compositions that are protective in cerebral ischemia (stroke). The present invention provides compositions and methods for preventing or treating cerebral ischemia, such as for example, by reducing neuronal cell death, reducing tissue edema, and/or reducing cognitive dysfunction associated with a cerebral ischemic disorder or reducing other symptoms and/or conditions associated with a cerebral ischemic condition, such as, for example, reducing infarct size, tissue edema or cognitive disorder associated with the presence of micro-emboli or a hypoxic condition.

The present invention provides gamma-tocopherol enriched tocopherol compositions, beta-tocopherol enriched tocopherol compositions and delta-tocopherol enriched compositions and methods for using such compositions. In preferred embodiments, the gamma-tocopherol enriched tocopherol compositions of the present invention comprise at least 50% gamma-tocopherol, at least 55% gamma-tocopherol, at least 60% gamma-tocopherol, at least 65% gamma-tocopherol, at least 70% gamma-tocopherol, at least 75% gamma-tocopherol, at least 80% gamma-tocopherol, at least 85% gamma tocopherol, at least 90% gamma-tocopherol, at least 95% gamma-tocopherol and at least 98% gamma-tocopherol. Gamma-tocopherol enriched tocopherol compositions comprise less than 50% alpha-tocopherol, less than 45% alpha-tocopherol, less than 40% alpha-tocopherol, less than 35% alpha-tocopherol, less than 30% alpha-tocopherol, less than 25% alpha-tocopherol, less than 20% alpha-tocopherol, less than 15% alpha-tocopherol, less than 10% alpha-tocopherol or less than 5% alpha-tocopherol. In some embodiments, gamma-tocopherol enriched tocopherol compositions comprise gamma-tocopherol as the sole active ingredient. As used herein, an "active ingredient" is one that is able to treat or prevent cerebral ischemia in a mammalian subject. In preferred embodiments, an active ingredient is able to reduce neuronal damage associated with cerebral ischemia at least about 30%, at least about 40%, at least about 50%, at least about 60%, at least about 70%, at least about 80%, at least about 80%, and even more preferably at least about 90%, in experimental models such as those described herein.

In additional preferred embodiments, a gamma-tocopherol enriched tocopherol composition comprises gamma-tocopherol in an amount effective to reduce neuronal cell death, reduce infarct size, reduce tissue edema associated with the cerebral ischemic condition, and/or reduce cognitive dysfunction and may further comprise a gamma-tocopherol metabolite and/or derivative and may further comprise alpha-tocopherol, beta-tocopherol and/or delta-tocopherol, and/or other ingredients. In other preferred embodiments, the gamma-tocopherol enriched tocopherol compositions of the present invention comprise additional active ingredients, and/or additional non-tocopherols. In some embodiments of gamma-tocopherol enriched tocopherol compositions, the gamma-tocopherol and additional ingredient(s) provide a synergistic effect. Gamma-tocopherol and an additional ingredient are considered to be synergistic when their combined effect is greater than additive of the individual effects.

In preferred embodiments, the beta-tocopherol enriched tocopherol compositions of the present invention comprise at least 50% beta-tocopherol, at least 55% beta-tocopherol, at least 60% beta-tocopherol, at least 65% beta-tocopherol, at least 70% beta-tocopherol, at least 75% beta-tocopherol, at least 80% beta-tocopherol, at least 85% beta tocopherol, at least 90% beta-tocopherol, at least 95% gamma-tocopherol and at least 98% beta-tocopherol. Beta-tocopherol enriched tocopherol compositions comprise less than 50% alpha-tocopherol, less than 45% alpha-tocopherol, less than 40% alpha-tocopherol, less than 35% alpha-tocopherol, less than 30% alpha-tocopherol, less than 25% alpha-tocopherol, less than 20% alpha-tocopherol, less than 15% alpha-tocopherol, less than 10% alpha-tocopherol or less than 5% alpha-tocopherol. In some embodiments, beta-tocopherol enriched tocopherol compositions comprises beta-tocopherol as the sole active ingredient. In additional preferred embodiments, a beta-tocopherol enriched tocopherol composition comprises beta-tocopherol in an amount effective to reduce neuronal cell death, reduce infarct size, reduce tissue edema associated with the cerebral ischemic condition, and/or reduce cognitive dysfunction and may further comprise a beta-tocopherol metabolite and/or derivative and may further comprise alpha-tocopherol, gamma-tocopherol and/or delta-tocopherol and/or other ingredients. In other preferred embodiments, the beta-tocopherol enriched tocopherol compositions of the present invention comprise additional active ingredients, and/or additional non-tocopherols. In some embodiments of beta-tocopherol enriched tocopherol compositions, the beta-tocopherol and additional ingredient(s) provide a synergistic effect. Beta-tocopherol and an additional ingredient are considered to be synergistic when their combined effect is greater than additive of the individual effects.

In preferred embodiments, the delta-tocopherol enriched tocopherol compositions of the present invention comprise at least 50% delta-tocopherol, at least 55% delta-tocopherol, at least 60% delta-tocopherol, at least 65% delta-tocopherol, at least 70% delta-tocopherol, at least 75% delta-tocopherol, at least 80% delta-tocopherol, at least 85% delta tocopherol, at least 90% delta-tocopherol, at least 95% gamma-tocopherol and at least 98% delta-tocopherol. Delta-tocopherol enriched tocopherol compositions comprise less than 50% alpha-tocopherol, less than 45% alpha-tocopherol, less than 40% alpha-tocopherol, less than 35% alpha-tocopherol, less than 30% alpha-tocopherol, less than 25% alpha-tocopherol, less than 20% alpha-tocopherol, less than 15% alpha-tocopherol, less than 10% alpha-tocopherol or less than 5% alpha-tocopherol. In some embodiments, delta-tocopherol enriched tocopherol compositions comprise delta-tocopherol as the sole active ingredient. In additional preferred embodiments, a delta-tocopherol enriched tocopherol composition comprises delta-tocopherol in an amount effective to reduce neuronal cell death, reduce infarct size, reduce tissue edema associated with the cerebral ischemic condition, and/or reduce cognitive dysfunction and may further comprise a delta-tocopherol metabolite and/or derivative and may further comprise alpha-tocopherol, beta-tocopherol and/or gamma-tocopherol and/or other ingredients. In other preferred embodiments, the delta-tocopherol enriched tocopherol compositions of the present invention comprise additional active ingredients, and/or additional non-tocopherols. In some embodiments of delta-tocopherol enriched tocopherol compositions, the delta-tocopherol and additional ingredient(s) provide a synergistic effect. Delta-tocopherol and an additional ingredient are considered to be synergistic when their combined effect is greater than additive of the individual effects.

Assays for measuring the effect of gamma-tocopherol enriched tocopherol compositions, beta-tocopherol enriched compositions and delta-tocopherol compositions are provided herein and are known to those of skill in the art.

In other aspects the present invention provides gamma-tocopherol metabolite or derivative enriched compositions, beta-tocopherol metabolite or derivative enriched compositions, and delta-tocopherol metabolite or derivative enriched compositions, and methods for using such compositions. In preferred embodiments, the gamma-tocopherol metabolite, beta-tocopherol metabolite or delta-tocopherol metabolite enriched compositions of the present invention comprise at least 50% gamma-, beta-, or delta-tocopherol metabolite or derivative, at least 55% gamma-, beta-, or delta-tocopherol metabolite or derivative, at least 60% gamma-, beta-, or delta-tocopherol metabolite or derivative, at least 65% gamma-, beta-, or delta-tocopherol metabolite or derivative, at least 70% gamma-, beta-, or delta-tocopherol metabolite or derivative, at least 75% gamma-, beta-, or delta-tocopherol metabolite or derivative, at least 80% gamma-, beta-, or delta-tocopherol metabolite or derivative, at least 85% gamma-, beta-, or delta-tocopherol metabolite or derivative, at least 90% gamma-, beta-, or delta-tocopherol metabolite or derivative and at least 95% gamma-, beta-, or delta-tocopherol metabolite or derivative. Gamma-tocopherol, beta-tocopherol or delta-tocopherol metabolite enriched compositions comprises less than 50% alpha-tocopherol, less than 45% alpha-tocopherol, less than 40% alpha-tocopherol, less than 35% alpha-tocopherol, less than 30% alpha-tocopherol, less than 25% alpha-tocopherol, less than 20% alpha-tocopherol, less than 15% alpha-tocopherol, less than 10% alpha-tocopherol or less than 5% alpha-tocopherol. In some embodiments, gamma-, beta-, or delta-tocopherol metabolite or derivative enriched compositions comprise the gamma-, beta-, or delta-tocopherol metabolite or derivative as the sole active ingredient. In additional preferred embodiments, a gamma-, beta-, or delta-tocopherol metabolite or derivative enriched composition comprises the gamma-, beta-, or delta-tocopherol metabolite or derivative in an amount effective to reduce neuronal cell death, reduce infarct size, reduce tissue edema associated with the cerebral ischemic condition, and/or reduce cognitive dysfunction. A gamma-, beta-, or delta-tocopherol metabolite or derivative enriched composition may further comprise tocopherol(s). In other preferred embodiments, the gamma-tocopherol, beta-tocopherol or delta-tocopherol metabolite or derivative enriched compositions of the present invention comprise additional active ingredients, and/or additional non-tocopherols. In some embodiments of gamma-, beta-, or delta-tocopherol metabolite or derivative enriched compositions, the gamma-, beta-, or delta-tocopherol metabolite or derivative and additional ingredient(s) provide a synergistic effect. A gamma-, beta-, or delta-tocopherol metabolite or derivative and an additional ingredient are considered to be synergistic when their combined effect is greater than additive of the individual effects. Assays for measuring the effect of gamma-, beta-, or delta-tocopherol metabolite or derivative enriched compositions are provided herein and are known to those of skill in the art.

In illustrative embodiments disclosed herein a gamma-tocopherol enriched tocopherol composition and a gamma-tocopherol metabolite enriched composition are shown to reduce total infarct at the time of MCAO and at the time of reperfusion, as described in Example 2. In further illustrative embodiments shown herein, a beta-tocopherol enriched tocopherol composition is shown to reduce total infarct size at three hours pre-MCAO when administered gavage and a delta-tocopherol enriched composition is shown to reduce total infarct size at the time of MCAO when administered IV.

Definitions

"Cerebral Ischemia" or "cerebral ischemic" or "a cerebral ischemic condition" refer to a medical event which is pathological in origin, or to a surgical intervention which is imposed on a subject, wherein circulation to a region of the brain is impeded or blocked, either temporarily, as in vasospasm or transient ischemic attach (TIA) or permanently, as in thrombolic occlusion. The affected region is deprived of oxygen and nutrients as a consequence of the ischemic event. This deprivation leads to the injuries of infarction or in the region affected. Ischemia occurs in the brain during, for example, a thromboembolic stroke, hemorrhagic stroke, cerebral vasospasm, head trauma, cardiac arrest, severe blood loss due to injury or internal hemorrhage and other similar conditions that disrupt normal blood flow. It may also occur after a head trauma, since the pressure caused by edema presses against and flattens the arteries and veins inside the brain, thereby reducing their ability to carry blood through the brain. Cerebral ischemia may also occur as a result of macro-or micro-emboli, such as may occur subsequent to cardiopulmonary bypass surgery.

By "tocopherol" is meant any of a family of molecules (including both tocopherols and tocotrienols and derivatives thereof) which are characterized by a 6-chromanol ring structure and a side chain at the 2 position. A "gamma-tocopherol enriched tocopherol composition", "beta-tocopherol enriched tocopherol composition" or a "delta-tocopherol enriched tocopherol composition" as used herein refers to the particular tocopherol as being enriched with respect to total tocopherols in the composition. Tocopherols possess a 4',8',12'-trimethyltridecyl phytol side chain, and the tocotrienols differ by the presence of double bonds at the 3', 7' and 11' positions of the side chain. As used herein, the term "tocopherol" encompasses, but is not limited to:

alpha-tocopherol, [2R-2R*(4R*,8R*)]-3,4-dihydro-2,5,7,8-tetramethyl-2-(4,8,12-trimethyltridecyl)-2H-1-benzopyran-6-ol; 2,5,7,8-tetramethyl-2-(4',8',12'-trimethyltridecyl)-6-chromanol; 5,7,8-trimethyltocol, Fernholz (1937) *J. Am. Chem. Soc.* 59:1154 and 60:700;

beta-tocopherol, 3,4-dihydro-2,5,8-trimethyl-2-(4,8,12-trimethyltridecyl)-2H-1-benzopyran-6-ol; 2,5,8-trimethyl-2-(4,8,12-trimethyltridecyl)-6-chromanol; 5-8-dimethyltocol; cumotocopherol; neotocopherol; p-xylotocopherol;

gamma-tocopherol, 3,4-dihydro-2,7,8-trimethyl-2-(4,8,12-trimethyltridecyl)-2H-1-benzyopyran-6-ol; 2,7,8-trimethyl-2-(4,8,12-trimethyltridecyl)-6-chromanol; 7,8-dimethyltocol; o-xylotocopherol;

delta-tocopherol, [2R-[2R*(4R*,8R*)]]-3,4-dihydro-2,8-dimethyl-2-(4,8,12-trimethyltridecyl)-2H-1-benzopyran-6-ol; 8-methyltocol;

epsilon-tocopherol, [R-(E,E)]-3,4-dihydro-2,5,8-trimethyl-2-(4,8,12-trimethyl-3,7,11-tridecatrienyl)-2H-1-benzopyran-6-ol; 2,5,8-trimethyl-2-(4,8,12-trimethyltrideca-3,7,11-trienyl)chroman-6-ol; 5-methyltocol;

$zeta_1$-tocopherol, 3,4-dihydro-2,5,7,8-tetramethyl-2-(4,8,12-trimethyl-3,7,11-tridecatrienyl)-2H-1-benzopyran-6-ol; 2,5,7,8-tetramethyl-2-(4,8,12-trimethyl-3,7,11-tridecatrienyl)-6-chromanol; 5,7,8-trimethyltocotrien-3',7',11'-ol;

$zeta_2$-tocopherol, 3,4-dihydro-2,5,7-trimethyl-2-(4,8,12-trimethyltridecyl)-2H-1-benzopyran-6-ol; 2,5,7-trimethyl-2-(4,8,12-trimethyltridecyl-6-chromanol; 5,7-dimethyltocol; and eta-tocopherol, 3,4-dihydro-2,7-dimethyl-2-(4,8,12-trimethyltridecyl)-2H-1-benzopyran-6-ol; 2,7-dimethyl-2-(4,8,12-trimethyltridecyl)-6-chromanol; 7-methyltocol. See *The Merck Index* (1996), Twelfth Edition, Merck & Co., Whitehouse Station, N.J., pp. 1620–1621 and 1712, and references cited therein. Other tocopherols include $xi_1$-, $xi_2$-, and sigma-tocopherols.

Derivatives of these compounds include, but are not limited to, salts, including but not limited to succinate, nicotinate, allophanate, acetate, and phosphate salts of the tocopherols described herein. Salts also include pharmaceutically acceptable salts. Derivatives include halogenated derivatives. Derivatives also include quinone derivatives and prodrug forms of tocopherols, such as those described in U.S. Pat. No. 5,114,957. Additional tocopherols and derivatives thereof are described in, e.g., U.S. Pat. Nos. 5,606,080 and 5,235,073. Preparation of various tocopherols are described in, e.g., U.S. Pat. Nos. 5,504,220, 4,978,617, and 4,977,282. Various tocopherols are available from Sigma Chemical Co., St. Louis, Mo.

The term "γ-CEHC" refers to the 2,7,8-trimethyl-2-(β-carboxy-ethyl)-6-hydroxy chroman, having a molecular weight of 264. This compound is a metabolite of γ-tocopherol and its synthesis and properties are described in U.S. Pat. No. 6,083,982, incorporated herein by reference (where it is also referred to as "LLU-alpha"). γ-CEHC may be in the racemic form or as the S enantiomer. A general discussion of the isolation and characterization of γ-CEHC is provided by Wechter et al. (U.S. Pat. No. 6,150,402).

The term "γ-CEBC" refers to the compound the 2,7,8-trimethyl-2-(β-carboxy-butyl)-6-hydroxy chroman, having a molecular weight of about 278. It may also be present in racemic form or as pure isomer(s).

By "gamma-tocopherol derivative" is meant gamma.-tocopherol metabolites and synthetic chroman derivatives including, but not limited to, γ-CEHC, γCEBC, racemic chromans, chroman methyl esters, chroman esters, chroman amides, R.sub.4 chroman esters, oxidized chroman derivatives, racemic 2,5,7,8-tetramethyl-2-(.beta.-carboxyethyl)-6-hydroxy chroman, and the like. Additional derivatives were defined by Wechter (U.S. Pat. No. 6,083,982.

"Tocopherol metabolites and derivatives" include, for example, 2,5,7,8-tetramethyl-2-(.beta.-carboxyethyl)-chroman, 2,7,8-trimethyl-2-(.beta.-carboxyethyl)chroman, racemic 4-methyl-6-(5,6-dimethylbenzohinoyl)-4-hexanolid, 4-Methyl-6-(3,5,6-trimethylbenzochinoyl)4-hexanolid, (S)-4-Methyl-6-(5,6-dimethylbenzochinoyl)-4-hexanolid, 2,7,8-Trimethyl-2-(.beta.-carboxyethyl)-6-acetyl chroman, 2,7,8-Trimethyl-2-(.beta.-carboxyethyl)-6-acetyl chroman methyl ester, and benzodipyran methyl ester, as well as γ-CEHC and γ-CEBC, described above, and compounds shown in FIG. 3 herein. Other gamma.-tocopherol metabolites and synthetic chroman derivatives may be known by those of skill in the art or will be discovered in the future and are encompassed by this definition.

In the body of a subject, gamma-tocopherol, beta-tocopherol and delta-tocopherol break down into metabolites, including for example, the metabolites described in Wechter et al. U.S. Pat. Nos. 6,150,402; 6,083,982; 6,048,891 and 6,242,479, specifically incorporated herein in their entirety. In particular, the present invention encompasses the use of gamma-tocopherol enriched tocopherol compositions that further comprise gamma-tocopherol metabolites such as gamma-CEHC, racemic gamma-CEHC and (S) gamma-CEHC. The general structure of other tocopherol metabolites are shown in FIG. 3. The present invention also encompasses the use of gamma-tocopherol metabolite enriched compositions that further comprise gamma-tocopherol.

By a "non-alpha" tocopherol enriched tocopherol composition is meant a composition that is enriched in, i.e., that comprises 50% or greater, a tocopherol other than alpha-tocopherol. Examples of non-alpha tocopherol enriched tocopherol compositions include without limitation, beta-tocopherol enriched tocopherol compositions, beta-tocopherol metabolite enriched compositions, delta-tocopherol enriched tocopherol compositions, delta-tocopherol metabolite enriched compositions, gamma-tocopherol enriched tocopherol compositions, gamma-tocopherol metabolite enriched compositions, epsilon-tocopherol enriched tocopherol compositions, zeta-tocopherol enriched tocopherol compositions, etc.

By a "non-tocopherol" is meant any compound which is not a tocopherol, tocotrienol, or derivative thereof, or the like.

"Infarct" or "infarction" relates to a region of a tissue or organ subjected to ischemia and suffering the physiological sequelae of ischemia. Infarction results from a sudden insufficiency of arterial or venous blood supply due to, for example, emboli, thrombi, vascular torsion or pressure that produces a macroscopic area of necrosis. Infarction also relates to a region injured as a result of exposure to a hemorrhage.

By "increasing cerebral blood flow is meant the act of improving clinical outcome by inducing a statistically or physiologically significant increase in cerebral blood flow in a treated subject relative to an untreated subject as determined using techniques which are well known in the art, such as vascular imaging, for example.

By "reducing infarct size" is meant the act of improving clinical outcome by inducing a statistically or physiologically significant reduction in infarct size in a treated subject relative to an untreated subject as determined using techniques which are well known in the art, such as vascular imaging, for example.

By "non-naturally-occurring composition" is meant a composition which is not found in this form in nature. A non-naturally-occurring composition can be derived from a naturally-occurring composition, e.g., as non-limiting examples, via purification, isolation, concentration, chemical modification (e.g., addition or removal of a chemical group), and/or, in the case of mixtures, addition or removal of ingredients or compounds. Alternatively, a non-naturally-occurring composition can comprise or be derived from a non-naturally-occurring combination of naturally-occurring compositions. Thus, a non-naturally-occurring composition can comprise a mixture of purified, isolated, modified and/or concentrated naturally-occurring compositions, and/or can comprise a mixture of naturally-occurring compositions in forms, concentrations, ratios and/or levels of purity not found in nature.

"Agents" or "cytoprotective agents" are defined herein as compounds, mixtures, or formulations of compounds which are capable of preventing or treating cerebral ischemia, such as by reducing neuronal damage or symptoms thereof, associated with a cerebral ischemic condition and/or cell damage due to cerebral ischemia. "Amelioration" means the prevention, reduction, palliation, or a counter-acting of the negative aspects of an ischemic condition or ischemic state. Amelioration does not require a complete recovery or complete prevention of the cerebral ischemic condition. A compound or agent may provide protective activity prior to, simultaneous with and/or after the cerebral ischemic event has occurred.

A "nutritional composition" is a composition that comprises naturally occurring components, preferably found in the food supply, that can be sold over the counter, as supplements, functional foods or food ingredients ie, without a physician's prescription. A pharmaceutical composition is one that includes ethical pharmaceuticals and which requires a physician's prescription for administration. A nutritional composition will comprise a tocopherol to be administered in a range of about 1 to about 50 mg per kg body weight of said mammalian subject. A pharmaceutical composition will comprise a tocopherol to be administered in a range of about 1 to about 1000 mg per kg body weight of said mammalian subject.

As used herein, an agent is said to be "cytoprotective" or to have "cytoprotective property" or "cytoprotective activity" if administration of the agent reduces and/or ameliorates symptoms of a cerebral ischemic condition and/or injury(ies) suffered by cells, tissues, organs and/or organisms that is induced secondary to cerebral ischemia. Cytoprotective activity and injury can be quantified in assays which measure results of injury such as death and inhibition of metabolic activity; these can be measured, for example, using appropriate fluorescent dyes, measuring enzyme activity and/or measuring intact cellular membrane in effected tissues by staining with appropriate indicators. Cytoproiective agents include cytoprotective tocopherols, metabolites thereof and derivatives thereof.

A "synergist" is defined as an agent or compound which when present results in a greater-than-additive increase, augmentation or enhancement of the effect of an agent or compound. In some cases, it may be difficult to determine which compound in a mixture is of primary importance and which only secondary. Thus, in a synergistic mixture of compounds, any of the active compounds within the mixture can be considered a synergist. A composition comprising "synergistic activity" or a "synergistic mixture" is a combination of compounds wherein the combined effect is greater than additive of the individual effects. Synergism may be apparent only at some ranges or concentrations.

By "amounts effective to reduce neuronal damage associated with a cerebral ischemic conditions and/or symptoms due to cerebral ischemia" is meant that the cytoprotective agent or agents (e.g., gamma-tocopherol, and/or beta-tocopherol, and/or delta tocopherol and/or a mixture thereof and/or derivatives and/or metabolites thereof) is present in a final concentration sufficient for reducing injury(ies) associated with a cerebral ischemic condition and/or symptoms due to cerebral ischemia. This amount includes, but is not limited to, a concentration which acts as a complete prophylaxis or treatment for a symptom of neuronal damage. An "effective amount" is an amount sufficient to effect beneficial or desired results. An effective amount can be administered in one or more administrations. For purposes of this invention, an effective amount of a cytoprotective composition is an amount that is sufficient to ameliorate, stabilize, reverse, slow or delay the progression of injury(ies) in mammalian subjects i) at risk for a cerebral ischemic condition, or ii) associated with, due to and/or symptoms of a cerebral ischemic condition. Preferably, amelioration of injury(ies) due to a cerebral ischemic condition can be quantified by an assay measuring, for example, reduction in cell death and/or enzyme inactivity and/or reduction of tissue edema and/or reduction in cognitive disorder and/or reducing infarct size, for example. In the case of injuries associated with a cerebral ischemic condition, the size and/or severity of an infarct in the brain of the subject may be determined, for example, by various noninvasive radiological procedures and/or by various symptomatic and diagnostic procedures known to those of skill in the art, such as magnetic resonance imaging (MRI), computerized tomography (CT) scan, and the like. Injuries associated with a cerebral ischemic condition also include cerebral edema and injuries that are associated with such edema. When used in relation to a cerebral ischemic condition, the term "effective" when describing a dose size, frequency, or duration, or the concept of dose "effectiveness," relates to a dosing which results in a reduction in the size and severity of an actual cerebral infarct, or to a probability that any such cerebral infarct, were it to occur, would be of reduced size and severity. Amelioration is preferably at least about 30%, preferably at least about 50%, more preferably at least about 70%, even more preferably at least about 80%, and even more preferably at least about 90% reduction in neuronal damage.

"Hypoxia," which is defined broadly as a condition under which a particular cell, organ or tissue receives an insufficient oxygen supply to allow normal function. More specifically, hypoxia can be measured as an average or mean environmental oxygen saturation level of less than 90%. Hypoxia is a direct result of ischemia since whenever blood supply is cut off, oxygen supply is also cut off. However, hypoxia can occur in other conditions, even if blood flow remains unaltered, including, but not limited to, carbon monoxide poisoning, drowning, suffocation and other forms of asphyxia.

The term "energetically-competent" refers to cells, cell lines or organisms which undergo aerobic respiration (oxidative metabolism). "Energetic incompetence" refers to the quality of cells incapable of undergoing aerobic respiration; such cells only perform anaerobic respiration (fermentation).

A "mammalian subject" includes, but is not limited to, a human, a farm animal, a sport animal, and a pet.

By "treatment" or "treating" is meant any treatment of a disease or disorder, in a mammal, including: preventing or protecting against the disease or disorder, that is, causing, the clinical symptoms of the disease not to develop; inhibiting the disease, that is, arresting or suppressing the development of clinical symptoms; and/or relieving the disease, that is, causing the regression of clinical symptoms.

"As used herein, the term "comprising" and its cognates are used in their inclusive sense; that is, equivalent to the term "including" and its corresponding cognates.

General Methods

General techniques for chemical manipulations are known in the art and are generally described in, for example, Haugland (1996) *Handbook of Fluorescent Probes and Research Chemicals*, Sixth Edition, Molecular Probes, Inc.; Carruthers (1986) *Some Modern Methods of Organic Synthesis*, Third Edition, Cambridge University Press; and Warren (1978) *Designing Organic Syntheses*, John Wiley & Sons, Ltd. Molecular biology techniques are generally described in, for example, Sambrook et al. (1989), *Molecular Cloning: A Laboratory Manual*, Second Edition; and Ausubel et al., eds. (1987) *Current Protocols In Molecular Biology*. Reagents useful in applying these techniques are widely known in the art and commercially available from a number of vendors.

Compositions

Provided herein are gamma-tocopherol enriched tocopherol compositions comprising gamma-tocopherol that may further comprise gamma-tocopherol metabolites, and/or gamma-tocopherol derivatives and/or other tocopherols, eg, beta- and delta-tocopherol, for use as cytoprotectants against damage, injury(ies) and/or symptoms associated with cerebral ischemia. Also provided herein are gamma-tocopherol metabolite enriched compositions comprising gamma-tocopherol metabolite(s) that may further comprise gamma-tocopherol, and/or derivatives thereof, and/or other tocopherol metabolites, for use as cytoprotectants against damage, injury(ies) and/or symptoms associated with cerebral ischemia.

Provided herein are beta-tocopherol enriched tocopherol compositions comprising beta-tocopherol that may further comprise beta-tocopherol metabolites, and/or beta-tocopherol derivatives, and/or other tocopherols, eg, gamma- and delta-tocopherol for use as cytoprotectants against damage, injury(ies) and/or symptoms associated with cerebral ischemia. Also provided herein are beta-tocopherol metabolite enriched compositions comprising beta-tocopherol metabolite(s) that may further comprise beta-tocopherol, and/or derivatives thereof, and/or other tocopherol metabolites, for use as cytoprotectants against damage, injury(ies) and/or symptoms associated with cerebral ischemia.

Provided herein are delta-tocopherol enriched tocopherol compositions comprising delta-tocopherol that may further comprise delta-tocopherol metabolites, and/or delta-tocopherol derivatives, and/or other tocopherols, eg gamma- and beta-tocopherol, for use as cytoprotectants against damage, injury(ies) and/or symptoms associated with cerebral ischemia. Also provided herein are delta-tocopherol metabolite enriched compositions comprising delta-tocopherol metabolite(s) that may further comprise delta-tocopherol, and/or derivatives thereof, and/or other tocopherol metabolites, for use as cytoprotectants against damage, injury(ies) and/or symptoms associated with cerebral ischemia.

These compounds are present in the compositions in amounts effective to ameliorate the injury(ies) and/or symptoms associated with cerebral ischemia. Preferably gamma-tocopherol enriched compositions comprise at least 50% gamma-tocopherol, at least 55% gamma-tocopherol, at least 60% gamma-tocopherol, at least 65% gamma-tocopherol, at least 70% gamma-tocopherol, at least 75% gamma-tocopherol, at least 80% gamma-tocopherol, at least 85% gamma tocopherol, at least 90% gamma-tocopherol and at least 95% gamma-tocopherol. Gamma-tocopherol enriched tocopherol compositions may also comprise gamma-tocopherol derivative(s) and/or gamma tocopherol metabolite(s), and/or other tocopherol(s) and/or mixtures thereof. Gamma-tocopherol enriched tocopherol compositions comprises less than 50% alpha-tocopherol, less than 45% alpha-tocopherol, less than 40% alpha-tocopherol, less than 35% alpha-tocopherol, less than 30% alpha-tocopherol, less than 25% alpha-tocopherol, less than 20% alpha-tocopherol, less than 15% alpha-tocopherol, less than 10% alpha-tocopherol or less than 5% alpha-tocopherol.

Preferably, gamma-tocopherol metabolite enriched compositions comprise at least 50% gamma-tocopherol metabolite, at least 55% gamma-tocopherol metabolite, at least 60% gamma-tocopherol metabolite, at least 65% gamma-tocopherol metabolite, at least-70% gamma-tocopherol metabolite, at least 75% gamma-tocopherol metabolite, at least 80% gamma-tocopherol metabolite, at least 85% gamma tocopherol metabolite, at least 90% gamma-tocopherol metabolite and at least 95% gamma-tocopherol metabolite. In preferred embodiments, gamma-tocopherol metabolite enriched compositions comprises less than 50% alpha-tocopherol, less than 45% alpha-tocopherol, less than 40% alpha-tocopherol, less than 35% alpha-tocopherol, less than 30% alpha-tocopherol, less than 25% alpha-tocopherol, less than 20% alpha-tocopherol, less than 15% alpha-tocopherol, less than 10% alpha-tocopherol or less than 5% alpha-tocopherol. Gamma-tocopherol metabolite enriched compositions may also comprise gamma-tocopherol and/or a gamma tocopherol derivative(s), and/or other tocopherol(s) and/or mixtures thereof.

Preferably beta-tocopherol enriched compositions comprise at least 50% beta-tocopherol, at least 55% beta-tocopherol, at least 60% beta-tocopherol, at least 65% beta-tocopherol, at least 70% beta-tocopherol, at least 75% beta-tocopherol, at least 80% beta-tocopherol, at least 85% beta tocopherol, at least 90% beta-tocopherol and at least 95% beta-tocopherol. Beta-tocopherol enriched tocopherol compositions may also comprise beta-tocopherol derivative(s) and/or beta tocopherol metabolite(s), and/or other tocopherol(s) and/or mixtures thereof. Beta-tocopherol enriched tocopherol compositions comprises less than 50% alpha-tocopherol, less than 45% alpha-tocopherol, less than 40% alpha-tocopherol, less than 35% alpha-tocopherol, less than 30% alpha-tocopherol, less than 25% alpha-tocopherol, less than 20% alpha-tocopherol, less than 15% alpha-tocopherol, less than 10% alpha-tocopherol or less than 5% alpha-tocopherol.

Preferably, beta-tocopherol metabolite enriched compositions comprise at least 50% beta-tocopherol metabolite, at least 55% beta-tocopherol metabolite, at least 60% beta-tocopherol metabolite, at least 65% beta-tocopherol metabolite, at least 70% beta-tocopherol metabolite, at least 75% beta-tocopherol metabolite, at least 80% beta-tocopherol metabolite, at least 85% beta tocopherol metabolite, at least 90% beta-tocopherol metabolite and at least 95% beta-tocopherol metabolite. In preferred embodiments, beta-tocopherol metabolite enriched compositions comprises less than 50% alpha-tocopherol, less than 45% alpha-tocopherol, less than 40% alpha-tocopherol, less than 35% alpha-tocopherol, less than 30% alpha-tocopherol, less than 25% alpha-tocopherol, less than 20% alpha-tocopherol, less than 15% alpha-tocopherol, less than 10% alpha-tocopherol or less than 5% alpha-tocopherol. Beta-tocopherol metabolite enriched compositions may also comprise beta-tocopherol and/or a beta tocopherol derivative(s), and/or other tocopherol(s) and/or mixtures thereof.

Preferably delta-tocopherol enriched compositions comprise at least 50% delta-tocopherol, at least 55% delta-tocopherol, at least 60% delta-tocopherol, at least 65% delta-tocopherol, at least 70% delta-tocopherol, at least 75% delta-tocopherol, at least 80% delta-tocopherol, at least 85% delta tocopherol, at least 90% delta-tocopherol and at least 95% delta-tocopherol. Delta-tocopherol enriched tocopherol compositions may also comprise delta-tocopherol derivative(s) and/or delta tocopherol metabolite(s), and/or other tocopherol(s) and/or mixtures thereof. Delta-tocopherol enriched tocopherol compositions comprises less than 50% alpha-tocopherol, less than 45% alpha-tocopherol, less than 40% alpha-tocopherol, less than 35% alpha-tocopherol, less than 30% alpha-tocopherol, less than 25% alpha-tocopherol, less than 20% alpha-tocopherol, less than 15% alpha-tocopherol, less than 10% alpha-tocopherol or less than 5% alpha-tocopherol.

Preferably, delta-tocopherol metabolite enriched compositions comprise at least 50% delta-tocopherol metabolite, at least 55% delta-tocopherol metabolite, at least 60% delta-tocopherol metabolite, at least 65% delta-tocopherol metabolite, at least 70% delta-tocopherol metabolite, at least 75% delta-tocopherol metabolite, at least 80% delta-tocopherol metabolite, at least 85% delta tocopherol metabolite, at least 90% delta-tocopherol metabolite and at least 95% delta-tocopherol metabolite. In preferred embodiments, delta-tocopherol metabolite enriched compositions comprises less than 50% alpha-tocopherol, less than 45% alpha-tocopherol, less than 40% alpha-tocopherol, less than 35% alpha-tocopherol, less than 30% alpha-tocopherol, less than 25% alpha-tocopherol, less than 20% alpha-tocopherol, less than 15% alpha-tocopherol, less than 10% alpha-tocopherol or less than 5% alpha-tocopherol. Delta-tocopherol metabolite enriched compositions may also comprise delta-tocopherol and/or a delta tocopherol derivative(s), and/or other tocopherol(s) and/or mixtures thereof.

Figure 2:
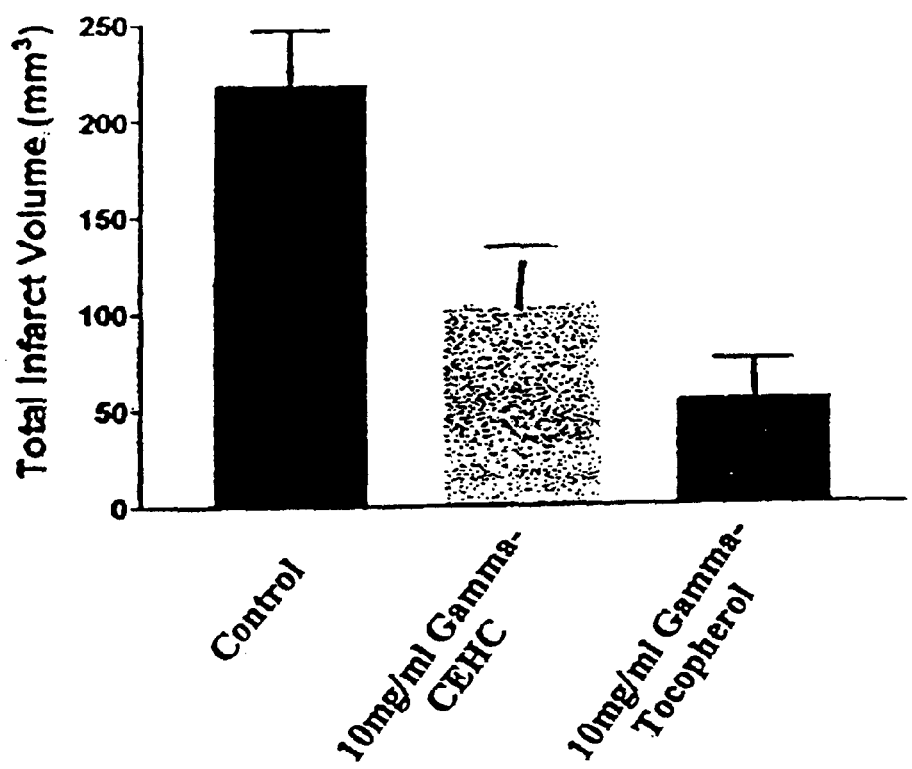
FIG. 2 shows the effect of gamma-tocopherol and its metabolite, gamma-CEHC, on the volumetric comparison of total infarct with administration of gamma-tocopherol and gamma-CEHC at reperfusion as described in Example 2.
Figure 4:
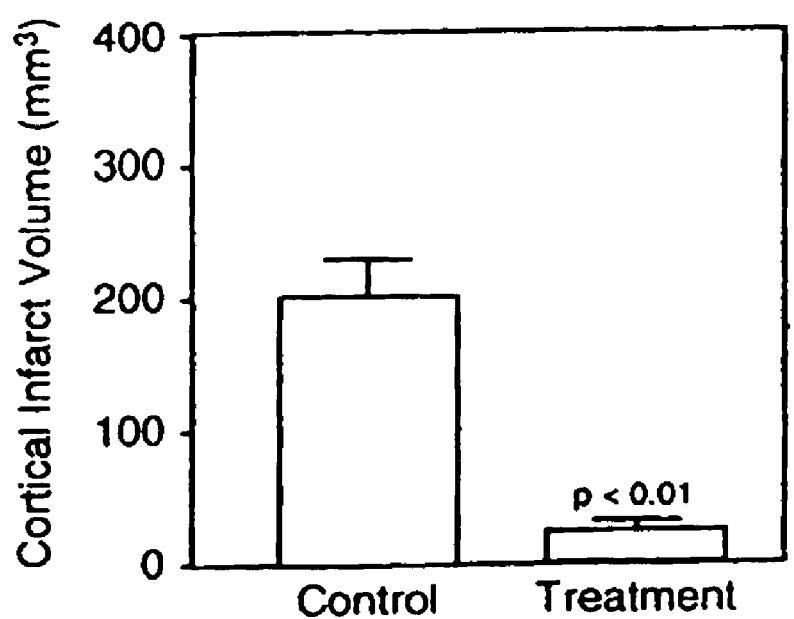
FIG. 4 shows the effect of gamma-tocopherol on stroke protection as measured in cerebral ischemia MCAO model.

In illustrative examples disclosed herein, a gamma-tocopherol enriched composition (obtained from Sigma and comprising greater than 97% gamma-tocopherol) and a gamma-tocopherol metabolite enriched composition, gamma-CEHC (greater than 98% gamma-CEHC) are able to reduce total infarct size when administered at the time of MCAO and when administered at reperfusion (see Example 2 and FIGS. 1 and 2, respectively). In additional experiments, total infarct size was measured for various tocopherol containing compositions at MCAO and reperfusion as measured by the assay described in Example 2. A gamma-tocopherol enriched composition comprising greater than 97% gamma-tocopherol and administered IV at 6 mg/kg, at MCAO was able to reduce infarct size by 82% whereas an alpha-tocopherol containing composition comprising greater than 99% alpha-tocopherol administered at 6 mg/kg at MCAO was able to reduce infarct by 42%. In additional experiments it was shown that for administration at MCAO, a gamma-tocopherol enriched composition was able to reduce infarct size by 81% when administered IV at 0.60 mg/kg and a delta-tocopherol containing composition comprising greater than 90% delta tocopherol when administered IV at 0.60 mg/kg was able to reduce infarct size by 52%. In additional experiments, it was shown that for administration at 3 hours pre-MCAO, a gamma-tocopherol enriched composition was able to reduce infarct size by 77% when administered by gavage at 10.00 mg/kg and a beta-tocopherol containing composition (obtained from Matreys, Inc. Pleasant Gap, Pa. and comprising greater than 90% beta-tocopherol) when administered gavage at 10.00 mg/kg was able to reduce infarct size by 76%. It was also shown that gamma-CEHC enriched composition decreased neuronal damage by 50–65% in drug ranges 0.1–5 mg/kg when administered IV at MCAO.

Tocopherols are chemical entities which, in general, contain a 6-chromanol ring structure and a side chain at the 2-position. Prototypical tocopherols include alpha-, beta-, gamma- and delta-tocopherol. However, as is known in the art, tocopherols and their derivatives can vary by the number and position of alkyl groups, double bonds and other substituents and variations on the ring and side chain. An "alkyl" is a cyclic, branched or straight chain chemical group containing only carbon and hydrogen, such as methyl, butyl and octyl. Alkyl groups can be either unsubstituted or substituted with one or more substituents, e.g., halogen, alkoxy, acyloxy, amino, hydroxyl, mercapto, carboxy, or benzyl. Alkyl groups can be saturated or unsaturated at one or several positions. Typically alkyl groups will comprise 1 to 8 carbons, preferably 1 to 6, and more preferably 1 to 4 carbon atoms. Additional tocopherols can be constructed by conjugation to the ring structure or side chain of various other moieties, such as those containing oxygen, nitrogen, sulfur and/or phosphorus. Tocopherol derivatives can also be made, as known in the art, by modifying the length of the side chain from that found in prototypical tocopherols such as alpha-, beta-, delta- and gamma-tocopherol. Tocopherols can also vary in stereochemistry and saturation of bonds in the ring structure and side chain. Additional tocopherol derivatives, including prodrugs, can be made by conjugation of sugars or other moieties to the side chain or ring structure; these can serve any of a number of functions, including increasing solubility and increasing functional activity of the tocopherol. Thus, as is understood in the art, the invention encompasses the use of tocopherol derivatives in which substitutions, additions and other alterations have been made in the 6-chromanol ring and/or side chain, with the proviso that the derivatives maintain at least one functional activity of a tocopherol, such as antioxidant activity or ability to counteract sterility in animals. The tocopherols have the general formula:

Tocopherols:

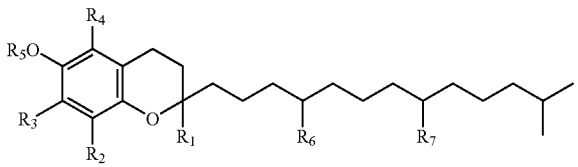

R1=CH3 with S or R configuration
R6=CH3 with S or R configuration
R7=CH3 with S or R configuration
R5=H or CH3 or acetate or succinate

|  | R2 | R3 | R4 |
|---|---|---|---|
| Gamma | CH3 | CH3 | H |
| Beta | CH3 | H | CH3 |
| Delta | CH3 | H | H |

Gamma-tocopherol metabolites and derivatives are disclosed in Wechter et al., U.S. Pat. Nos. 6,150,402; 6,083,982 and 6,048,891. Other tocopherol metabolites or derivatives include tocotrienols, naturally occurring analogs of tocopherols and metabolites having the general formulas as shown below. Other metabolites are shown in FIG. 3.

Tocotrienols:

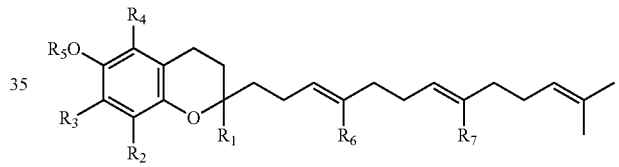

R1=CH3 with S or R configuration
R6=CH3 with S or R configuration
R7=CH3 with S or R configuration
R5=H or CH3 or acetate or succinate

|  | R2 | R3 | R4 |
|---|---|---|---|
| Gamma | CH3 | CH3 | H |
| Beta | CH3 | H | CH3 |
| Delta | CH3 | H | H |

Natural Compounds: Some Naturally Occurring Chromene Analogs of Tocopherols are Disclosed in WO00056348A1.

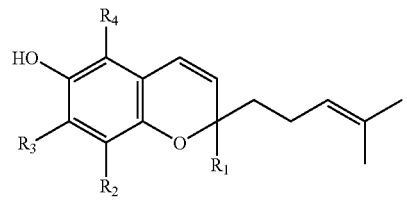

R1=CH3 with S or R configuration
R2, R3, R4=H or CH3

Examples of metabolites and derivatives include those of Formula 1, below (substituted chromans):

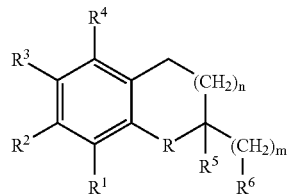

in which:

R is O, S, SO, SO$_2$, a secondary or tertiary amine group, a phosphate group, a phosphoester group, or an unsubstituted or substituted methylene group;

R$^1$ and R$^2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-membered aliphatic or aromatic ring;

R$^3$ and R$^4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-membered aliphatic, aromatic or heterocyclic ring;

R$^5$ is H, OH, alkyl, aryl, alkenyl, alkynyl, aromatic, ester or unsubstituted or substituted amine;

R$^6$ is COOH, COOR$^7$, CONH$_2$, CONHR$^7$, CONR$^7$R$^8$, NH$_2$, NHR$^7$, NR$^7$R$^8$, or a carboxylate salt;

R$^7$ and R$^8$ independently are unsubstituted or substituted alkyl, aryl, alkaryl, aralkyl, alkenyl or alkynyl;

n is 0 to 3; and m is 0 to 5. In preferred embodiments of Formula I, R is O. Also preferably, n=1, m=2, R$^6$ is COOH, R$^3$ is H or OH, R$^4$ is H or CH$_3$. In a preferred embodiment, R$^1$, R$^2$ and R$^5$ are CH$^3$.

Exemplary compounds include:

R is O, R$^1$, R$^2$, and R$^5$ are CH$_3$, R$^3$ is OH, R$^4$ is H or CH$^3$, R$^6$ is COOH, n=1 and m=2. (where R$^4$ is H, this is gamnma-CEHC).

Other exemplary compounds of Formula 1 includes those in which R is O, R$^1$, R$^2$, and R$^5$ are CH$_3$, R$^3$ is H, R$^4$ is H or CH$^3$, R$^6$ is COOH, n=1 and m=2. (where R4 is H, this is 2,7,8-trimethyl-2-(β-carboxyethyl)-chroman).

In a preferred embodiment, R$^7$ is a C$_{1-6}$ alkyl group, in particular CH$_3$. In another preferred embodiment, R$^3$ is OH.

Specific examples of gamma-tocopherol metabolites include for example, gamma-CEHC: synonyms: 6-hydroxy-2,7,8-trimethylchroman-2-propanoic acid and 2,7,8-trimethyl-2-(β-carboxyethyl)-6-hydroxy chroman, and having formula:

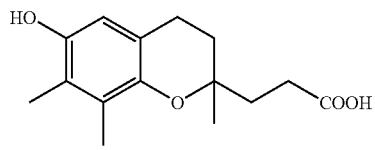

(S)-Gamma-CECH

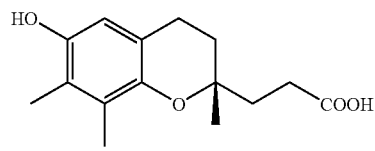

Racemic 2,5,7,8-Tetramethyl-2-(β-carboxyethyl)-6-hydroxy Chroman

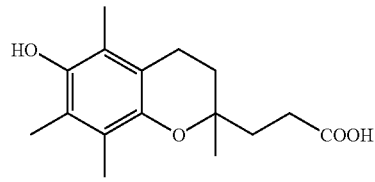

Racemic 2,5,7,8-Tetramethyl-2-(β-carboxyethyl)-chroman

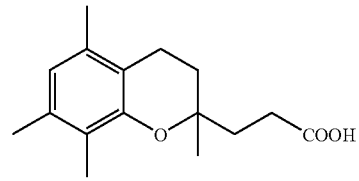

Racemic 2,7,8-Trimethyl-2-(β-carboxyethyl)-6-acetyl Chroman

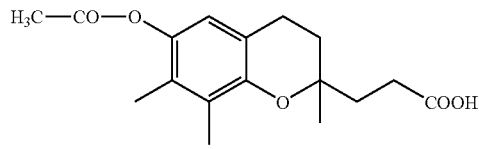

Racemic 2,7,8-Trimethyl-2-(β-carboxyethyl)-6-acetyl Chroman Methyl Ester

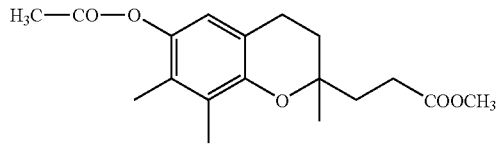

Racemic 2,7,8-Trimethyl-2-(β-carboxyethyl)-6-hydroxy Chroman Methyl Ester

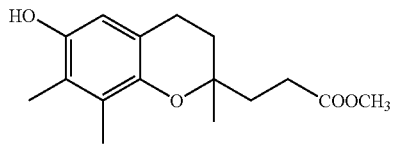

Racemic 2,7,8-Trimethyl-2-(β-carboxyethyl)chroman

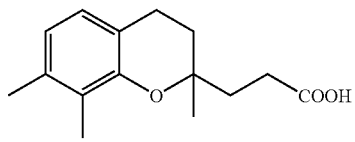

Racemic 4-Methyl-6-(5,6-dimethylbenzochinoyl)-4-hexanolid

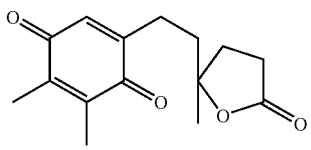

(R)-4-Methyl-6-(5,6-dimethylbenzochinoyl)-4-hexanolid

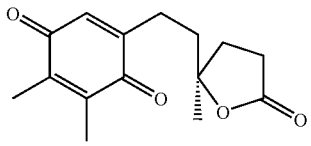

(S)-4-Methyl-6-(5,6-dimethylbenzochinoyl)-4-hexanolid

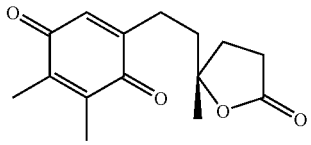

4-Methyl-6-(3,5,6-trimethylbenzochinoyl)-4-hexanolid

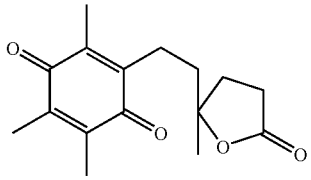

Benzodipyran Methyl Ester

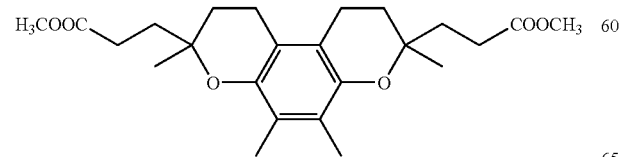

Examples of metabolites and derivatives include those of Formula II, below:

Formula II:

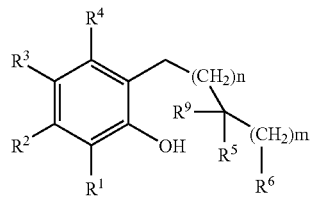

wherein $R^1$ and $R^2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-membered aliphatic or aromatic ring;

$R^3$ and $R^4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-membered aliphatic, aromatic or heterocyclic ring;

$R^5$ is H, OH, alkyl, aryl, alkenyl, alkynyl, aromatic, ester or unsubstituted or substituted amine;

$R^6$ is COOH, $COOR^7$, $CONH_2$, $CONHR^7$, $CONR^7R^8$, $NH_2$, $NHR^7$, $NR^7R^8$, or a carboxylate salt;

$R^7$ and $R^8$ independently are unsubstituted or substituted alkyl, aryl, alkaryl, aralkyl, alkenyl or alkynyl;

$R^9$ is hydroxyl or unsubstituted or substituted alkoxyl;

n is 0 to 3; and m is 0 to 5.

In preferred embodiments, $R^1$, $R^2$ and $R^5$ are $CH_3$ and preferably, $R^3$ is OH and $R^4$ preferably is H. Additionally, it is preferred that n=1 and referred that m=2.

In a further preferred embodiment, $R^6$ is $COOCH_2CH_3$ and $R^9$ is OH. In another preferred embodiment, $R^6$ is COOH and $R^9$ is $CH_3CH_2O$. Specific exemplary examples include

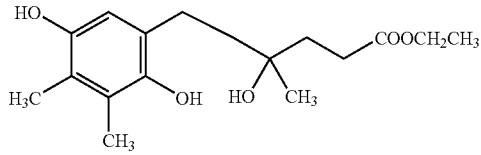

Examples of metabolites and derivatives include those of Formula III, below

Formula III:

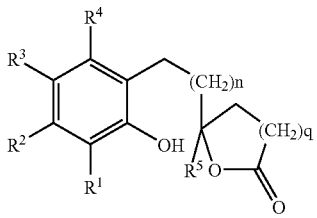

wherein $R^1$ and $R^2$ independently are H, OH, alkyl, aryl, alkenyl, alkynyl, aromatic, ether, ester, unsubstituted or substistituted sulfonyl, or jointly complete a 5- or 6-membered aliphatic or aromatic ring;

$R^3$ and $R^4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-membered aliphatic, aromatic or heterocyclic ring;

$R^5$ is H, OH, alkyl, aryl, alkenyl, alkynyl, aromatic, ester or unsubstituted or substituted amine;

n is 0 to 3; and q is 0 to 4.

In preferred embodiments, n=1. Also in preferred embodiments, q=2.

Exemplary compounds of Formula III include the following:

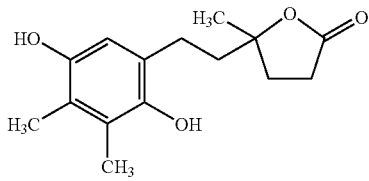

Examples of metabolites and derivatives include those of Formula IV, below

Formula IV:

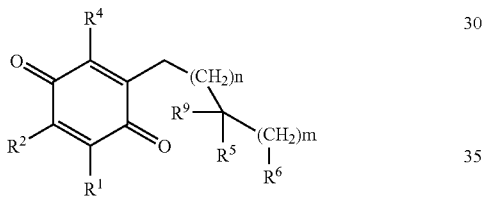

wherein $R^1$ and $R^2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-membered aliphatic or aromatic ring;

$R^4$ is H, OH, alkyl, aryl, alkenyl, alkynyl, aromatic, ether, ester, unsubstituted or substituted amine, amide, halogen or unsubstituted or substituted sulfonyl;

$R^5$ is H, OH, alkyl, aryl, alkenyl, alkynyl, aromatic, ester or unsubstituted or substituted amine;

$R^6$ is COOH, $COOR^7$, $CONH_2$, $CONHR^7$, $CONR^7R^8$, $NH_2$, $NHR^7$, $NR^7R^8$, or a carboxylate salt;

$R^7$ and $R^8$ independently are unsubstituted or substituted alkyl, aryl, alkaryl, aralkyl, alkenyl or alkynyl;

$R^9$ is hydroxyl or unsubstituted or substituted alkoxyl;

n is 0 to 3; and m is 0 to 5.

In preferred embodiments, n=1 and m=2.

Exemplary compounds according to Formula IV include:

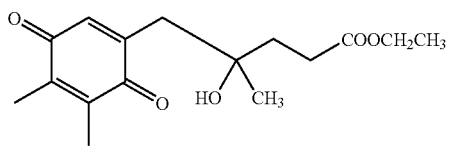

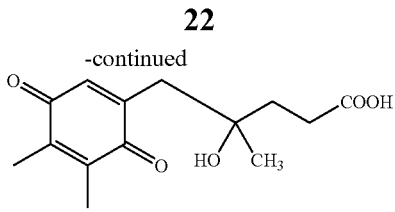

Examples of metabolites and derivatives include those of Formula V, below

Formula V:

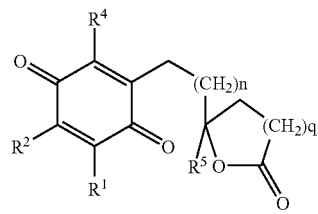

$R^1$ and $R^2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-membered aliphatic or aromatic ring;

$R^4$ is H, OH, alkyl, aryl, alkenyl, alkynyl, aromatic, ether, ester, unsubstituted or substituted amine, amide, halogen or unsubstituted or substituted sulfonyl;

$R^5$ is H, OH, alkyl, aryl, alkenyl, alkynyl, aromatic, ester or unsubstituted or substituted amine;

n is 0 to 3; and q is 0 to 4. In preferred embodiments, n=1 and q=2.

Exemplary compounds of Formula V include:

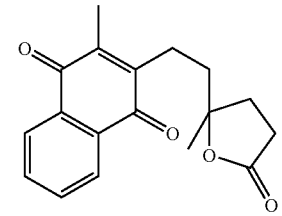

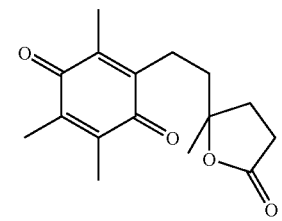

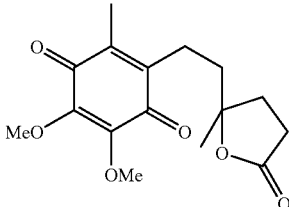

When compounds of Formula II–V are derived from the corresponding compounds and then oxidized, a preferred embodiment is $R^4$=H, $R^5$ is not $CH_3$.

In preferred embodiments of the present invention, gamma-tocopherol enriched tocopherol compositions include for example:

gamma-tocopherol enriched composition comprising greater than 90% gamma-tocopherol and more preferably greater than 95% gamma-tocopherol;

gamma-CEHC enriched composition comprising greater than 90% gamma-CEHC and preferably greater than 95% gamma-CEHC;

gamma-tocopherol enriched composition comprising gamma-CEHC;

gamma-tocopherol enriched composition for intravenous injection comprising at least 50% gamma-tocopherol and delta-tocopherol;

gamma-tocopherol enriched composition for gavage administration comprising at least 50% gamma-tocopherol and beta-tocopherol;

beta-tocopherol compositions comprising greater than 90% beta-tocopherol and more preferably, greater than 95% beta-tocopherol; and delta-tocopherol compositions comprising greater than 90% delta-tocopherol and more preferably greater than 95% delta-tocopherol.

Activity of a gamma-, beta-, or delta-tocopherol enriched tocopherol composition or a gamma-, beta, or delta-tocopherol metabolite enriched composition can be experimentally tested, for example, in an assay which measures ability to ameliorate injury(ies) or damage associate with a cerebral ischemic condition. Such assays (which are detailed in Examples) include without limitation the use of hippocampal cell assay, animal cerebral infarct assay and animal assay for behavioral recovery after cerebral ischemia. Gamma-, beta-, or delta-tocopherol enriched tocopherol compositions and gamma-, beta-, or delta-tocopherol metabolite enriched compositions suitable for the present invention include those which are capable of ameliorating injury(ies) associated with a cerebral ischemic condition, as indicated, for example, by a reduction in neuronal cell death, reduction in tissue edema associated with a cerebral ischemic condition, reduction in infarct size, reduction in cognitive disorder as measured by the methods disclosed in the Examples. Reduction in neuronal damage associated with a cerebral ischemic condition is quantified at least about 30%, preferably at least about 50%, more preferably at least about 70%, even more preferably at least about 80%, and even more preferably at least about 90% reduction.

It is well known that gamma-tocopherol is metabolized in vivo to form, for example, gamma-CEHC and gamma-CEBC, among other metabolites. In humans, this metabolite is thought to be the result of sequential oxidation of its phytyl sidechain by enzymes that catalyze omega and beta oxidation. Therefore a further aspect of the present invention includes methods of treatment in which the patient is treated with agents effective to induce such oxidation, such as, for example, inducers of the enzyme cytochrome P450. Such inducers and methods are known in the art.

In the present invention, a nutritional composition will comprise a tocopherol to be administered in a range of about 1 to about 50 mg per kg body weight of said mammalian subject. In additional embodiments, a nutritional composition will comprise a tocopherol to be administered at a lower limit of at least about 1.00, 1.50, 2.00, 2.50, 5.00, 7.50, 10.00, 12.50, 15.00, 17.50, 20.00, 22.25, and 25.00 mg per kg body weight of said mammalian subject and at an upper limit of not greater than about 27.25, 30.00, 32.50, 35.00, 37.25, 40.00, 42.25, 45.00, 47.25, and 50.00 mg per kg body weight of said mammalian subject, with the lower limit and upper limit to be selected independently. A pharmaceutical composition will comprise a tocopherol to be administered in a range of about 1 to about 1000 mg per kg body weight of said mammalian subject. In additional embodiments, a pharmaceutical composition will comprise a tocopherol to be administered at a lower limit of at least about 1, 10, 20, 30, 40, 50, 60, 70, 80, 90, 100, 200, 300, 400, and 500 mg per kg body weight of said mammalian subject and at an upper limit of not greater than about 60, 70, 100, 200, 300, 400, 500, 600, 700, 800, 900, and 1000 mg per kg body weight of said mammalian subject, with the lower limit and upper limit to be selected independently. In additional embodiments, a pharmaceutical composition will comprise a tocopherol to be administered in a range of about 10 to about 100 mg per kg body weight of said mammalian subject.

Methods of Using Compounds of the Invention

The compositions of the present invention are administered to a subject in amounts to reduce neuronal cell damage. The subject may be experiencing a cerebral ischemic condition, experiencing symptoms associated with or due to a cerebral ischemic condition or be at risk for a cerebral ischemic condition.

In one aspect, methods of the present invention relate to preventing neuronal damage in a mammalian subject at risk of developing injury due to a cerebral ischemic condition, e.g. for example, by an infarct in the brain. The methods of reducing neuronal damage relate to minimizing the extent and/or severity of injury in the brain associated with or due to a cerebral ischemic condition by ameliorating or reducing the injury that would otherwise occur. The methods encompass administering a gamma-tocopherol enriched tocopherol composition and/or a beta-tocopherol enriched tocopherol composition and/or a delta-tocopherol enriched tocopherol composition and/or a gamma-, beta-, or delta-tocopherol metabolite enriched composition(s) to a subject. The amount administered and the duration of the treatment are effective to minimize the size and/or severity of the neuronal damage in the mammalian subject as measured by for example, reduction in neuronal cell death and/or reduction in tissue edema associated with a cerebral ischemic condition and/or reduction in cognitive disorder and/or reduction in infarct size. Thus, it is anticipated that as a result of such treatment the size and/or severity of any neuronal damage that develops is minimized.

The present invention provides prophylactic treatments for neuronal damage including cell death and/or presence of tissue edema and/or cognitive dysfunction and/or cerebral infarcts which may be due to ischemic, hypoxic/anoxic, or hemorrhagic events. Gamma-, beta-, or delta-tocopherol enriched tocopherol compositions and/or a gamma-, beta-, or delta-tocopherol metabolite enriched compositions of the present invention are administered to a subject at risk of experiencing neuronal damage associated or due to a cerebral ischemic condition, and ameliorates the severity of the damage, should it occur. The method is intended for a subject at risk of neuronal damage that is associated with, or results from, an acute or chronic medical condition. Such conditions might arise as a result of medical or surgical treatment planned for the subject (e.g., angioplasty) or as a result of an emergent medical condition such as a stroke or severe blood loss. Other conditions which place a subject at risk for neuronal damage associated with a cerebral ischemic condition include a genetic predisposition to stroke or a condition that is understood to increase the probability of incurring a cerebral infarct such as atherosclerosis, previous stroke or transient ischemic attacks, diabetes mellitus, hypertension, hypercholesterolemia, a history of smoking and may also include schizophrenia, epilepsy, neurodegenerative disorders, Alzheimer's disease and Huntington's disease. Diagnostic and/or pathological characterization of stroke victims has identified numerous additional medical conditions producing stroke that are widely known to practitioners of internal and neurological medicine.

Additional medical conditions that place a subject at risk for neuronal damage associated with or due to a cerebral ischemic condition include, but are not limited to, thrombosis; vasculitis (including collagen vascular disease (e.g., temporal (giant cell) arteritis, polyartefitis nodosa, Wegener's granulatosis, Takayasu's arteritis, syphilis), meningitis (e.g., tuberculosis, fungi, syphilis, bacteria, herpes zoster), arterial dissection (e.g., carotid, vertebral, intracranial arteries at the base of the brain), hematologic disorders (e.g., polycythemia, thrombocytosis, thrombotic, thrombocytopenic purpura, disseminated intravascular coagulation, dysproteinemias, hemogiobinopathies (sickle cell disease)) and that caused by cocaine, amphetamines, moyamoya disease, fibromuscular dysplasia and Binswanger's disease); embolism (including cardiac sources (e.g., dysrhythmia, coronary heart disease, rheumatic heart disease, etc.), coronoary artery bypass graft (CABG), atherothrombotic arterial sources (e.g., bifurcation of common carotid artery, carotid siphon, distal vertebral artery, aortic arch) and unknown sources (e.g., may be associated with a hypercoagulable state secondary to systemic disease, carcinoma (especially pancreatic), eclampsia, oral contraceptives, lupus, factor C or S deficiency, Factor V mutation such as Factor V Leiden, etc.)); vasoconstriction (including vasospasm (e.g., cerebral vasospasm following subarachnoid hemorrhage) and reversible cerebral vasoconstriction (e.g., idiopathic, migraine, eclampsia, trauma); and venous conditions (including dehydration, pencranial infection, postpartum and postoperative states and systemic cancer).

Medical conditions that place a subject at risk of neuronal damage associated with or due to a cerebral ischemic condition due to intracranial hemorrhage include, but are not limited to, spontaneous intracerebral hemorrhage (e.g., hypertensive, amyloid angiopathy); ruptured aneurysm (e.g., saccular, mycotic); ruptured arteriovenous malformation; drug use (e.g., cocaine, amphetamines); trauma; bleeding with brain tumors; systemic bleeding disorders (including anticoagulation therapy) and hemorrhagic infarction.

A nonhuman mammal is identified as a subject if the animal is to be subjected to procedures that induce cerebral ischemic condition and lead to for example, a cerebral infarction, or is to undergo surgical or invasive procedures comparable to those identified in the preceding paragraph for human subjects.

In the present invention, gamma-, beta-, or delta-tocopherol enriched tocopherol composition(s) and/or gamma-, beta-, or delta-tocopherol metabolite enriched composition(s) are administered to a mammalian subject. In the case where an individual has been diagnosed as having suffered an ischemic event, such as a stroke or a result of suffocation, the administration of a composition of the present invention should begin as soon as possible after the ischemic event occurred, preferably within a few days (e.g., within 1, 2 or 3 days), or more preferably within a few hours (e.g., less than about 12, 8, 6, 4, or 2 hours), of the event. In the case where an individual is at risk of developing an infarct as a result of impending surgical or similar intervention or is otherwise at high risk of infarction, administration of the compositions of the present invention preferably begins as soon as the decision planning the intervention is made or the risk identified. In either case, the duration of the treatment is a few days, several days, or a few weeks, circumscribed by the time frame in which ischemic injury is understood, or expected, to occur.

The size of the dose of the gamma-, beta-, or delta-tocopherol enriched tocopherol composition and/or gamma-, beta-, or delta tocopherol metabolite enriched composition and/or gamma-, beta-, or delta-tocopherol derivative composition to be administered depends on the route of administration and the medical condition of the subject, as well as, other individual parameters of the subject such as age, size and weight. Administration of the composition to an individual having suffered an ischemic event represents the most acute situation of those considered in this invention, since the ischemic event has already occurred and the need for immediate minimization of injury from infarction is extreme. This may necessitate a particular size of dose appropriate for the circumstances. A human subject or nonhuman animal scheduled for imminent surgery or medical intervention is in a somewhat less acute medical state. As a result the size of each dose may be different, and may be open to somewhat greater variation and still be within the practice of the invention. In general, the size of each dose for administration are described herein. Dose sizes for nonhuman mammals generally fall in the same range on a mg/kg basis.

For the reasons just summarized, the frequency of dosing may also vary. A more acute medical status may suggest a different dosing regime than one that is somewhat less acute. In general, the invention may be practiced by administering doses at a frequency ranging from about once or twice per week to about once daily.

Likewise for the reasons given above, the duration of dosing is subject to variability. For example, a stroke victim, being in an extremely acute medical condition, requires the effect of the method of the invention to be realized as early as possible. This clearly dictates a course of dosing that emphasizes a short duration. A subject facing scheduled surgery or medical intervention, or being otherwise at high risk for a stroke, having a less acute medical status, may be subjected to dosing for a different, generally longer, duration. In general, a victim of stroke may be administered the oral antigen for a duration ranging from about 3 days to about 10 days. On the other hand, a subject who is about to undergo medical or surgical treatment which enhances the risk of a cerebral ischemic condition in the brain may undergo dosing for a duration ranging from about 5 days to about 14 days. A subject who is at risk for developing a cerebral infarct associated with a chronic medical condition such as a genetic predisposition to stroke, diabetes mellitus, hypertension, hypercholesterolemia, and a history of smoking may be treated for a duration of at least 5 days.

The methods of the invention require the administration of gamma-, beta-, or delta-tocopherol enriched tocopherol compositions and/or gamma-, beta-, or delta-tocopherol metabolite enriched compositions and/or a derivative(s), thereof, or mixtures thereof, in an effective amount. With regard to a cerebral ischemic condition, an effective amount is one sufficient to reduce neuronal damage resulting from the cerebral ischemic condition. A reduction of neuronal damage is any prevention of injury to the brain which otherwise would have occurred in a subject experiencing a cerebral ischemic event absent the treatment of the invention. Several physiological parameters may be used to assess reduction of brain injury, including, but not limited to, a smaller infarct size, improved cerebral regional blood flow and decreased intracranial pressure, for example, as compared to pretreatment patient parameters, untreated cerebral ischemic patients or cerebral ischemic patients receiving a control alone. The size of an infarct in a human patient having suffered a stroke may be determined, for example, by various noninvasive radiological procedures known to those of skill in the field of medicine, especially to those of skill in radiology and neurology. Examples of methods available in the field include, but are not limited to, computerized tomography (CT) scanning, magnetic resonance imaging (MRI), ultrasonic imaging, and targeted radiotracer imaging. The size of an infarct in a nonhuman mammal having been subjected to procedures which have produced a cerebral infarct, may be determined by similar noninvasive procedures as those available for use with human patients. In addition, in cases where a nonhuman mammal dies in the course of an experiment, the size of the infarct may be established by direct observation, by post mortem anatomical and histological examination. Such procedures are well known to those of skill in the fields of veterinary medicine, pathology, physiology, anatomy, and related fields and an example of such a procedure is exemplified herein.

The severity of an infarct in a human patient having suffered a stroke may be determined, for example, by various symptomatic and diagnostic procedures known to those of skill in the fields of medicine, especially to those of skill in neurology, hematology, and physical medicine, in addition to assessing the results of radiological and anatomical diagnosis that were discussed in the preceding paragraph. Kinetic, sensory, and cognitive behavior is affected in stroke patients. Medical diagnosis routinely includes such assessments in analysis of the status of stroke victims. For example, the effectiveness of the various doses of the claimed compositions may be assessed using standard measurements known in the art including, but-not limited to, the Barthel Index, Modified Rankin Score, NIH Stroke Scale total, NIH Stroke Scale motor item, the number of days to discharge from the hospital, mortality and other neuropsychological battery scores.

In addition, stroke patients may be diagnosed by the methods of hematology. These may be used to assess the populations and cellular characteristics of immune cells in the circulation, as well as various enzymatic activities or cellular components from brain tissue. These activities or components are generally found in the blood of stroke victims but are typically absent or present at only low levels in subjects that have not suffered a stroke. Similar procedures may be applied to nonhuman mammals who have suffered ischemic injury as a result of medical or surgical procedures. The amounts or values of the various results obtained in these diagnostic tests may be evaluated with respect to values known in the various fields to represent normal or pathological states. As a result of evaluating the group of diagnostic results obtained as outlined above, the severity of the infarction may be assessed by workers of skill in the medical fields. The dose size, frequency, and the duration of treatment by the method of the present invention may be adjusted accordingly based on the severity of the infarction and the general medical condition of the patient.

The compositions, as described above, can be prepared as a medicinal preparation (such as an aqueous solution for injection) or in various other media, such as foods for humans or animals, including medical foods and dietary supplements. A "medical food" is a product that is intended for the specific dietary management of a disease or condition for which distinctive nutritional requirements exist. By way of example, but not limitation, medical foods may include vitamin and mineral formulations fed through a feeding tube or cancer or burn victims (referred to as enteral administration or gavage administration). A "dietary supplement" shall mean a product that is intended to supplement the human diet and is typically provided in the form of a pill, capsule, tablet or like formulation. By way of example, but not limitation, a dietary supplement may include one or more of the following ingredients: vitamins, minerals, herbs, botanicals; amino acids, dietary substances intended to supplement the diet by increasing total dietary intake, and concentrates, metabolites, constituents, extracts or combinations of any of the foregoing. Dietary supplements may also be incorporated into food stuffs, such as, functional foods designed to promote cerebral health or to prevent cerebral ischemia. If administered as a medicinal preparation, the composition can be administered, either as a prophylaxis or treatment, to a patient in any of a number of methods. The cytoprotective compositions may be administered alone or in combination with other pharmaceutical agents and can be combined with a physiologically acceptable carrier thereof. The effective amount and method of administration of the particular cytoprotective formulation can vary based on the individual subject, the stage of disease, and other factors evident to one skilled in the art. During the course of the treatment, the concentration of the subject compositions may be monitored to insure that the desired level is maintained.

Generally, the route(s) of administration useful in a particular application are apparent to one of skill in the art. Routes of administration include, but are not limited to, oral, topical, dermal, transdermal, transmucosal, epidermal, parenteral, gastrointestinal.

For in vitro or ex vivo administration, the compounds may be provided in the medium of the cells and/or organ, as a single bolus, by repetitive addition, by continual infusion, or the like.

For administration, the invention includes subject compositions suitable for oral administration including, but not limited to, pharmaceutically acceptable tablets, capsules, powders, solutions, dispersions, or liquids. For rectal administration, the subject compositions may be provided as suppositories, as solutions for enemas, or other convenient application. Otherwise, the subject compositions may be administered intravascularly, arterially or venous, subcutaneously, intraperitoneally, intraorganally, intramuscularly, or the like.

For administration, the formulations may conveniently be presented in unit dosage form and may be prepared by any methods well known in the art of pharmacy. Such methods include the step of bringing into association the active ingredients with the carrier which constitutes one or more accessory ingredients. In general, the formulations are prepared by uniformly and intimately bringing into association the active ingredients with liquid carriers or finely divided solid carriers or both, and then if necessary shaping the product.

For oral administration, suitable subject compositions include, but are not limited to, pharmaceutically acceptable tablets, capsules, powders, solutions, dispersions, or liquids. Also, the subject compositions may be compounded with other physiologically acceptable materials which can be ingested including, but not limited to, foods, including, but not limited to, food bars, beverages, powders, cereals, cooked foods, food additives and candies.

When the composition is incorporated into various media such as foods, it may simply be orally ingested. The food can be a dietary supplement (such as a snack or wellness dietary supplement) or, especially for animals, comprise the nutritional bulk (e.g., when incorporated into the primary animal feed).

The amount of the composition ingested, consumed or otherwise administered will depend on the desired final concentration. Typically, the amount of a single administration of the composition of the invention can be about 0.1 to about 1000 mg per kg body weight, or about 0.5 to about 10000 mg per day. Any of these doses can be further subdivided into separate administrations, and multiple dosages can be given to any individual patient. A typical dosage for vitamin E administration is 100–600 mg/kg/day for an adult human. However, various different dosages are described in scientific publications; see, for example, Ng et al. (1999) *Food Chem. Toxicol.* 37: 503–8; Ko et al. (1999) *Arch. Phys. Med. Rehabil.* 80: 964–7; Chen et al. (1999) *Prostaglandins Other Lipid Mediat.* 57: 99–111; and Thabrew et al. (1999) *Ann. Clin. Biochem.* 36: 216–20.

To determine the optimum concentration for any application, conventional techniques may be employed. Thus, for in vitro and ex vivo use, a variety of concentrations may be used and various assays employed to determine the degree of neuronal damage, such as, for example, measurements of cell death, infarct size, and cognitive dysfunction.

Formulations of the present invention adapted for oral administration may be presented as discrete units such as capsules, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredients may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethylcellulose), lubricant, inert diluent, preservative, disintegrant (e.g. sodium starch glycollate, cross-linked povidone, cross-linked sodium carboxymethylcellulose) surface-active or dispersing agent. Molded tablets may be made by moulding in a suitable machine a mixture of the powdered compound moistened with an inert liquid diluent. The tablets may optionally be coated or scored and may be formulated so as to provide controlled release of the active ingredients therein using, for example, hydroxypropylmethylcellulose in varying proportions to provide the desired release profile.

The subject compositions may be administered parenterally including intravascularly, arterially or venous, subcutaneously, intradermally, intraperitoneally, intraorganally, intramuscularly, or the like.

Formulations for parenteral administration include aqueous and non-aqueous isotonic sterile injection solutions which may contain buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

For topical administration, the subject compositions may be provided as a wide variety of product types including, but are not limited to, lotions, creams, gels, sticks, sprays, ointments and pastes. These product types may comprise several types of formulations including, but not limited to solutions, emulsions, gels, solids, and liposomes.

Compositions useful for topical administration of the compositions of the present invention formulated as solutions typically include a pharmaceutically-acceptable aqueous or organic solvent. The terms "pharmaceutically-acceptable organic solvent" refer to a solvent which is capable of having a gamma-, beta-, or delta-tocopherol composition and/or metabolite and/or derivative thereof, or mixtures thereof, dispersed or dissolved therein, and of possessing acceptable safety properties (e.g., irritation and sensitization characteristics). Examples of suitable organic solvents include: propylene glycol, polyethylene glycol (200–600), polypropylene glycol (425–2025), glycerol, 1,2,4-butanetriol, sorbitol esters, 1,2,6-hexanetriol, ethanol, isopropanol, butanetriol, sorbitol esters, 1,2,6-hexanetriol, ethanol, isopropanol, butanediol, and mixtures thereof.

If the topical compositions useful in the subject invention are formulated as an aerosol and applied to the skin as a spray-on, a propellant is added to a solution composition. Examples of propellants useful herein include, but are not limited to, the chlorinated, fluorinated an chloro-fluorinated lower molecular weight hydrocarbons.

Topical compositions useful in the subject invention may be formulated as a solution comprising an emollient. As used herein, "emollients" refer to materials used for the prevention or relief of dryness, as well as for the protection of the skin. A wide variety of suitable emollients are known and may be used herein.

Another type of product that may be formulated from a gamma-, beta-, delta; tocopherol enriched tocopherol composition and/or a gamma-, beta-, or delta-tocopherol metabolite enriched composition is a cream. Another type of product that may be formulated from a composition of the present invention is a lotion.

Yet another type of product that may be formulated from a composition of the present invention is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble.

Another type of formulation is an emulsion. Emulsifiers may be nonionic, anionic or cationic and examples of emulsifiers are described in, for example, U.S. Pat. Nos. 3,755,560, and 4,421,769.

Lotions and creams can be formulated as emulsions as well as solutions.

Single emulsions for topical preparations, such as lotions and creams, of the oil-in-water type and water-in-oil type are well-known in the art. Multiphase emulsion compositions, such as the water-in-oil-in-water type, are also known, as disclosed, for example, in U.S. Pat. No. 4,254,105. Triple emulsions are also useful for topical administration of the present invention and comprise an oil-in-water-in-silicone fluid emulsion as disclosed, for example in U.S. Pat. No. 4,960,764.

Another emulsion useful in the topical compositions is a micro-emulsion system. For example, such a system comprises from about 9% to about 15% squalane, from about 25% to about 40% silicone oil; from about 8% to about 20% of a fatty alcohol; from about 15% to about 30% of polyoxyethylene sorbitan mono-fatty acid (commercially available under the trade name TWEENS) or other nonionics; and from about 7% to about 20% water.

Liposomal formulations are also useful for the compositions of the present invention. Such compositions can be prepared by combining gamma-, beta, or delta-tocopherol, and/or metabolite thereof, and/or derivative thereof, and/or mixtures thereof, with a phospholipid, such as dipalmitoylphosphatidyl choline, cholesterol and water according to known methods, for example, as described in Mezei et al. (1982) *J. Pharm. Pharmacol.* 34:473–474, or a modification thereof. Epidermal lipids-of suitable composition for forming liposomes may be substituted for the phospholipid. The liposome preparation is then incorporated into one of the above topical formulations (for example, a gel or an oil-in-water emulsion) in order to produce the liposomal formulation. Other compositions and pharmaceutical uses of topically applied liposomes are described for, example, in Mezei (1985) *Topics in Pharmaceutical Sciences*, Breimer et al. eds., Elsevier Science, New York, N.Y., pp. 345–358.

For rectal administration, the subject compositions may be provided as solutions for enemas, as suppositories with a suitable base comprising, for example, cocoa butter or a salicylate, or as other convenient applications.

Formulation for vaginal administration may be presented as pessaries, tampons, creams, gels, pastes, foams or spray formulations containing in addition to the active ingredient such carriers as are known in the art to be appropriate.

To determine the optimum concentration for any application, conventional techniques may be employed. Thus, for in vitro and ex vivo use, a variety of concentrations may be used and various assays employed to determine the degree of dysfunction of the cells when exposed to stress. Examples of such assays are described herein and have been described, for example, in U.S. Pat. No. 5,801,159.

The above-mentioned compositions and methods of administration are meant to describe but not limit the methods and compositions of the present invention. The methods of producing various compositions and devices are within the ability of one skilled in the art and are not described in detail here.

The gamma-, beta-, or delta-tocopherol enriched tocopherol compositions, and/or gamma-, beta-, or delta-tocopherol metabolite enriched compositions, and methods using the compositions are capable of reducing neuronal damage associated with cerebral ischemia. These conditions can be induced experimentally by chemical interference or by changing the environmental conditions in the laboratory (e.g., by inducing anoxia, hypothermia, hyperthermia, etc.).

Various assays, compositions and methods useful for identifying compositions and methods for reducing neuronal damage are provided in the Examples.

The following examples are provided to illustrate, but not limit, the invention.

EXAMPLES

Example 1

Example 1 describes cell-based assays for determining the ability of a tocopherol composition to counteract ischemic-induced neuronal cell injury and cell death.

Insults to the brain that disrupt its blood supply, as in ischemia, or its oxygen supply, as in hypoxia (low oxygen) or anoxia (zero oxygen), rapidly cause neuronal imbalance leading to cell death (Flynn et al. (1989) Ischemia and Hypoxia, pp. 783–810, In: Basic Neurochemistry, Siegel et al. (Eds.), Raven Press, New York). Cerebral ischemic insults are modeled in animals by occluding vessels to, or within, the cranium (Molinari (1986) Experimental models of ischemic stroke, pp. 57–73, In: Stroke: Pathophysiology, Diagnosis and Management, Vol. 1, Barnett et al. (Eds.), Churchill Livingstone, N.Y.). In vitro models of ischemia use different means of oxygen and glucose deprivation. For example, by placing neuronal cultures into large anaerobic or hypoxic chambers and exchanging culture medium with oxygen-free and defined ionic composition media (Goldberg et al. (1990) *Stroke* 21:75–77). The toxic overstimulation of neuronal glutamate receptors, especially N-methyl-D-aspartate (NMDA) receptors, contribute to hypoxic-ischemic neuronal injury (Choi (1988) *Neuron* 1:623–634), ischemic induction of reactive oxygen species (ROS) (Watson et al. (1988) *Ann. NY Acad. Sci.* 59:269–281), excessive calcium influx (Grotta et al. (1988) *Stroke* 19:447–454), arachidonic acid increase (Siesjo (1981) *J. Cereb. Blood Flow Metab.* 1: 155–185), and DNA damage (MacManus et al. (1993) *Neurosci. Lett.* 164:89–92) causing a cascade of neurodegeneration.

Among various types of primary neuronal cultures, primary embryonic hippocampal neuronal culture is widely used for several reasons. The hippocampus is a source of a relatively homogenous population of neurons with well-characterized properties typical of central nervous system (CNS) neurons in general. Pyramidal neurons, the principal cell type in the hippocampus, have been estimated to account for 85% to 90% of the total neuronal population (Banker et al. (1998) Culturing Nerve Cells, $2^{nd}$ edition, The MIT Press, Cambridge, Mass.). Also, the hippocampus exhibits a remarkable capacity for activity-dependent changes in synaptic function, such as long-term potentiation (Hawkins et al. (1993). *Annu. Rev. Neurosci.* 16:625–665).

Hippocampal cultures typically are prepared from 18- to 19-day fetal rats. At this age, the generation of pyramidal neurons, which begins in the rat at about E15, is generally complete. The tissue is easy to dissociate, the meninges are removed readily, and the number of glial cells still is relatively,modest (Park et al. (2000) *J Neurochem* 74:114–124).

1A. Primary Cell Culture

The following protocol describes the procedure used to isolate and culture primary hippocampal neuronal cells from embryonic rat brain for use in the cell-based assays described herein.

Prior to cell isolation, long tip Pasteur pipettes with an opening of 1 mm, 0.4–0.5 mm, and 0.25 mm were fire-polished, cleaned with 70% ethanol, siliconized (Sigmacote, Sigma Chemical Cat. No. SL-2) and autoclaved. All other instruments for dissection were soaked in 70% ethanol at least 2 hr before the dissection. Also prior to cell isolation, culture flasks (T75 $cm^2$) and plates were coated with poly-D-lysine (Sigma Chemical, Cat. No. P-6407). For the coating, 50 µg/ml poly-D-lysine was added to the flask or plate (5 ml per T75 $cm^2$ flask and 50 µl/well in a 96 well plate) for one hour. The flask or plate was then washed twice with sterile, distilled water and allowed to air dry in a culture hood for one hour before use. HBSS (Ca—Mg free) was prepared as follows: 10.0 ml 10×HBSS (Hank's CMF—Gibco #310–4180), 3.3 ml 0.3 M HEPES, pH 7.3, 10 ml of 0.35% sodium bicarbonate, 1.0 ml Penicillin/Streptomycin (100×) and 1.0 ml 100 mM pyruvate were mixed with 74.7 ml $H_2O$ to make 100 ml of solution.

A pregnant rat (El 8–El 9) was euthanized with $CO_2$, and the uterus was removed. The embryos were removed from the sac, decapitated and their brains were removed. The brains were immersed in cold (4° C.) BSS (Ca/Mg free) in a small petri dish. A dish (100-mm) was covered with paraffin to make a better surface for the dissection. The hippocampi were removed from the brains under a dissecting i microscope and placed on the paraffin-covered dish. The meninges were stripped away and the dissected hippocampi were collected in a small petri dish in HBSS (Ca/Mg free).

The hippocampi from one litter were placed in a 15-ml centrifuge tube (generally 10–12 brains/litter), and the tube was filled with HBSS (Ca/Mg free). After centrifugation at 1000 rpm for 2 min using the desktop centrifuge, the supernatant was removed. 2 ml of HBSS (Ca/Mg free) was added to each tube and the tissue was triturated 2 times with a long tipped siliconized pipette with the three different opening sizes (total of 6–7 times). The trituration started with a pipette with a normal opening size, and then smaller (half of size), then one with the smallest hole. After centrifugation at 1000 rpm for 2 minutes, the supernatant was discarded and 2 ml of Neurobasal/B27i (with antibiotics) was added to each tube. Neurobasal/B27i media contains Neurobasal medium (Life Technologies Cat No. 21103–049) with 1×B27 supplement (Life Technologies Cat No. 17504–044), 0.5 µM L-glutamine, 25 µM L-glutamic acid, and 1×Penicillin/Streptomycin. The cells were triturated 1 time with a long tip siliconized pipette with three different opening sizes. The trituration started with a pipette with a normal opening size, then the smaller one (half of size) and finally the one with the smallest hole. Cell density was determined in a hemocytometer using the trypan blue exclusion method. A stock solution of 0.4% trypan blue in 0.9% NaCl was mixed one to one with a few drops of the cell suspension, and allowed to stand 4 minutes before counting the fraction of dye-excluding cells. A typical yield is $3 \times 10^5$–$6 \times 10^5$ cells/brain.

The desired number of viable cells were added to poly-D-lysine-coated 12-well plates, flasks or MetTek dishes in Neurobasal/B27i, and incubated in air atmosphere with 5% $CO_2$ at 37° C. The cells were generally seeded at a density of $1.5 \times 10^6$ cells per T75 cm$^2$ flask and at a density of ~100,000 cells per well of a 12-well plate. Each T75 cm$^2$ flask received 15 ml of medium and each well of a 12-well plate received 1 ml of medium.

After three to four days in culture, half the media was removed from each well or flask, and an equal amount of fresh Neurobasal/B27m medium (Neurobasal medium with 1×B27 supplement, 0.5 µM L-glutamine), which contains 5 µM cytosine arabinoside (AraC), was added. Seven to eight days from the initial culture, half the media was removed from each well or flask, and an equal amount of fresh Neurobasal/B27m medium (no Ara-C) was added.

1B. Cell Injury Assay

In the following assay, ischemia is induced by anoxia-reoxygenation in cultured hippocampal neuronal cells and test agents are accessed for their potency and/or efficacy against ischemic-induced neuronal cell injury and cell death. The assay protocol is diagramed as follows:

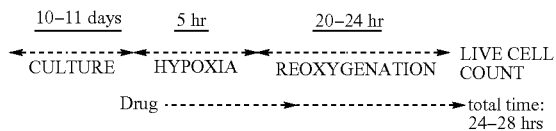

Primary hippocampal neuronal cells were prepared and plated on poly-D-lysine coated 12-well plates as described in Example 1A above. The cells were cultured for 10–11 days as described in Example 1A.

100 ml of LoG-Neurobasal medium in a T150 cm$^2$ flask was pre-equilibrated in the hypoxic chamber overnight and 20 ml of LoG-Neurobasal medium in a T75 cm$^2$ flask was pre-equilibrated in a standard incubator (5% $CO_2$) overnight. LoG-Neurobasal medium contains NoG-Neurobasal medium (no glucose) (Life Technologies, custom order) plus 0.5 mM glucose, 0.5 mM L-glutamine and 0.25×Penicillin/Streptomycin. 100 ml of Neurobasal/B27AO medium in a T150 cm$^2$ was pre-equilibrated in a standard incubator (5% $CO_2$) overnight. Neurobasal/B27AO medium contains Neurobasal medium (Life Technologies, Cat. No. 21103–049) with 2×B27 minus AO supplement (Life Technologies, Cat. No. 10889–038), 0.5 mM L-glutamine, and 0.25×Penicillin/Streptomycin.

The equilibrated 100 ml of LoG-Neurobasal in T150 cm$^2$ flask was removed from the hypoxic chamber, and the medium was lightly bubbled with 100% $N_2$ for 30 min. to deoxygenate completely. Existing culture medium (Neurobasal/B27m) was aspirated from the cultured cells in each 12-well plate using the vacuum pump with an attached sterile glass pasteur pipette. The cells were washed once with 2 ml of glucose free-BSS$_0$ (pH 7.4). Glucose free-BSS$_0$ (pH 7.4) contains 143.6 mM NaCl, 5.4 mM KCl, 1.8 mM $CaCl_2$, 0.8 mM $MgSO_4$, 1 mM $NaH_2PO_4$, 26.2 mM $NaHCO_3$, 10 mg/l phenol red and 0.25×Penicillin/Streptomycin.

The cultured neurons (10–11 days from initial culture) were replenished with deoxygenated LoG-Neurobasal (1 ml per well for each well of a 12-well plate). The test agents were added directly to each well (usually 3 concentrations of the compound plus positive control, each in triplicate). Generally, the test agents were dissolved in 100% DMSO. To reduce the DMSO effect on the cells, highly concentrated compounds were added in a small quantity (typically 200× concentration). The concentration of DMSO in the culture did not exceed 0.5%.

The plates were placed, with their lids left ajar, in the anaerobic chamber for 5 hours. For normoxia controls, pre-equilibrated normoxic LoG-Neurobasal medium was added to each well and the plate replaced in the standard incubator (5% $CO_2$) for 5 hours. After 5 hours of hypoxia, the culture media was carefully aspirated and 2 mL of new oxygenated (pre-equilibrated) Neurobasal/B27AO was added to each well. Reoxygenated medium was achieved by placing medium overnight in the culture incubator. The same test agents with same the concentrations were added back into the corresponding wells. The plates were placed in the cell culture incubator and reoxygenated for 20–24 hours. After reoxygenation for 20–24 hours, the number of live neurons were counted using the cell tracker green fluorescence method as follows. The culture medium was aspirated from each well of the 12-well plates and the neurons were washed once with 2 ml of HBSS (prewarmed to 30–37° C.; 25 mM HEPES, 100 mM NaCl, 5 mM KCl, 1.2 mM $MgCl_2$, 1.3 mM $CaCl_2$, 1.0 mM KH2PO4, pH 7.4, filter sterilized). 1 ml of 5 µM Cell Tracker Green fluorescent dye (Molecular Probes, Cat. No. 2925) dissolved in HBSS was added to the cells and the plates were placed in the dark at room temperature for 15 minutes. After washing the neurons once with 2 ml of HBSS, 1 ml of HBSS was added to each well, and fluorescent cells were counted using the fluorescent microscope.

In experiments carried out in support of the invention, gamma-tocopherol enriched tocopherol compositions and gamma-CEHC enriched compositions each provided at least 40% protection against hippocampal cell injury in the primary hippocampal cell model.

Example 2

Animal Cerebral Infarct Assay

This assay is used to assess the efficacy of the test agents in protecting the brain against necrosis following cerebral ischemia induced in rats. Middle Cerebral Artery Occlusion (MCAO) is a widely used technique to induce transient focal cerebral ischemia in animal models. It has been demonstrated that the rat model of MCAO is an appropriate approximation of ischemic damage in humans. Furthermore, this model accurately represents the involvement of middle cerebral artery (MCA), the most affected vessel in human stroke, and also allows reperfusion as it happens in humans. MCAO by a two-hour occlusion is used to produce the maximum size of cortical infarction without increased mortality at twenty-four hours.

2A. Middle Cerebral Artery Occlusion (MCAO)

Male Wistar rats (Hadan, Ind.) weighing 300–350 g were allowed free access to water and commercial rodent diet under standard laboratory conditions. The room temperature was maintained at 20–23° C. and room illumination was on a 12/12-hour light/dark cycle. The rats were acclimatized to the laboratory environment 5 to 7 days prior to the study.

Before surgery, the animals were fasted overnight, but had free access to water. The-rats were anesthetized with 3.0% isoflurane (Aerrane, Front Dodge, Iowa) in 0.8% oxygen and the animal's neck was shaved and sterilized before the operation. The animals were subjected to two hours MCAO using a modified intraluminal filament technique. A midline incision on the ventral part of the neck was made to expose external and internal carotid arteries. The right external and common carotid arteries were ligated by a suture (silk 5/0, Carlisle Laboratories, Farmers Branch, Tex.) and the right internal artery was temporarily ligated by a microvascular clip (Fine Science Tool Inc., Foster City, Calif.). A small incision was made in the common carotid artery and a nylon filament, its tip rounded by heating, prepared from a fishing line (Stren Fishing Lines, Wilmington, Del.) was inserted from the right common carotid artery. The filament was advanced into the internal carotid artery 18–20 mm from the point of bifurcation of internal and external arteries and a suture was tightly ligated around the filament. Two hours post occlusion, the animals were re-anesthetized to allow reperfusion for the remaining of the experiment by removal of the filament.

2B. Drug Administration

The following is a description of various ways by which gamma-tocopherol enriched tocopherol compositions and gamma-tocopherol metabolite enriched compositions are administered in this assay.

2B1. I.C.V. Infusion

The anesthetized animal were placed on a stereotaxic apparatus (Harvard Apparatus, S. Natick, Mass.). Anesthesia was maintained by inhalation of 3.0% isoflurane in 0.8% oxygen throughout the entire procedure. The scalp was shaved and sterilized prior to surgery. A midline sagittal incision about 3 cm long was made slightly behind the eyes to expose the skull. The skull was scraped with a rounded end spatula to remove periosteal connective tissue. A bur hole was placed 1.5 mm lateral, 1 mm posterior to the left of the bregma to mark the left lateral ventricle. A brain infusion cannula (ALZET CO. Palo Alto, Calif.) was inserted 4 mm deep into the hole. The desired depth was adjusted by attaching spacers to the cannula. The cannula was attached to a 4-cm silastic catheter (Helix Medical Inc.) fixed in place with dental cement (Ketac-cement, Norristown, Pa.). The catheter was either attached to a primed osmotic pump placed subcutaneously between the shoulder blades for permanent infusion or to a syringe for a short infusion.

2B2. I.V. Osmotic Pump Implantation Into the Jugular Vein

Anesthesia is maintained by inhalation of 3.0% isoflurane in 0.8% oxygen throughout the entire procedure. The animal's neck is shaved and sterilized before operation. A midline incision is made on the ventral part of the neck to exposes the jugular vein. The vein is isolated and ligated with a suture (silk 5/0, Carlisle Laboratories, Farmers Branch, Tex.) rostral to the point of the incision and a microvascular clip (Fine Science Tool Inc., Foster City, Calif.) close to the heart. A small incision is made between two ligations. A 2 cm silastic catheter (Helix Medical Inc) attached to a PE-60 tube (Becton. Dickinson and Co., Sparks, Md.) connected to an ALZET (ALZET CO. Palo Alto, Calif.) pump is introduced and advanced 2 mm into the jugular vein toward the heart. the microvascular clip is removed and the catheter is secured in place with a suture (silk 5/0, Carlisle Laboratories, Farmers Branch, Tex.). The pump is placed into a pocket made subcutaneously between the shoulder blades, allowing the catheter to reach over neck to the jugular vein with sufficient slack to permit free movement of neck and head.

2B3. I.V. Infusion via Femoral Vein

Anesthesia was maintained by inhalation of 3.0% isoflurane in 0.8% oxygen throughout the entire procedure. The exterior site of the right femoral vein was shaved and sterilized prior to surgery. A 3 cm incision was made in the right groin region and the femoral vein was isolated. A small incision was made on the femoral vein temporarily ligated with a microvascular clip to introduce and advance a polyethylene (PE-50) catheter (Becton. Dickinson and Co., Sparks, Md.). The catheter was secured in place with suture (silk 5/0, Cailisle Laboratories, Farmers Branch, Tex.). The other end of the catheter was attached to a syringe filled with the heparinized saline for the bolus injection. Using a hemostat a pocket was made subcutaneously on the back of the animal so the PE catheter can be brought up to the exteriorization point at the nape of the neck for either a bolus injection or a continuous injection by an osmotic pump.

2B4. I.P. Injection

An awake rat is held in a standard hand hold position, a 23¾ G needle is injected into the lower right quarter of the abdomen pass the peritoneum, slightly off the midline. To avoid organ injection, the plunger of the syringe is slightly pulled back. If no fluid is withdrawn, the content of the syringe is delivered into the abdominal cavity.

2B5. Gavage Feeding

A standard rat gavage tube (Popper & Sons Inc, NY) was attached to a 3-cc hypodermic syringe. The animal was held by the shoulder in a vertical position. The feeding tube was placed into the mouth then advanced until it reached the stomach (the approximate insertion length of the tube was measured prior to the feeding). The content of the syringe was slowly delivered, and then the tube is withdrawn.

2C. Behavioral Assessment

One hour after MCAO, the animal is gently held by its tail and observed for forelimb flexion. Then the animal is put on the floor and observed for walking pattern. Only an animal(s) scoring 3 on Bederson grading system (Table 1) is used for this study.

TABLE 1

Bederson grading system for neurological evaluation

| Neurological deficit | Grading | Behavioral observation |
|---|---|---|
| Normal | grade 0 | No observable deficit |
| Moderate | grade 1 | forelimb flexion |
| Severe | grade 2 | forelimb flexion, decreased resistance to lateral push |
| | grade 3 | forelimb flexion, decreased resistance to lateral push, circle to paretic side |

2D. Temperature Control

Body temperatures are controlled and maintained at 37.5° C.+/−1 degree via external heating and cooling devices. To lower the body temperature, animals are located in a cooling chamber which uses ice to cool circulating air. Throughout the study, the body temperature is recorded using a temperature transponder (BMDS Inc., Seaford, Del.) implanted subcutaneously at the time of MCAO between the rat shoulder blades and the body temperature is read via a pocket scanner (BMDS Inc., Seaford, Del.). Alternatively, the body temperature is taken by inserting the temperature probe into the animal's rectum. The body temperature is recorded every hour for 6 hours post occlusion; however, body temperatures are taken more frequently so that the animal is maintained at the normothermic temperature.

2E. Evaluation of Ischemic Damage

The animals are sacrificed by $CO_2$ asphyxiation (dry ice) 24 hours post-MCAO. The skull is removed to expose the brain using a small bone cutter and starting from the base of the skull. The brain is removed quickly, rinsed in a chilled saline and placed on a rat brain tissue slicer (ASI instrument, Mich.). Seven 2-mm thick coronal slices are cut from each brain using razor blades. The slices are immersed in 0.9% saline containing 1.0% 2,3,5-triphenyltetrazolume chloride (TTC) (Sigma Chemical Co., St. Louis, Mo.) and incubated in a 37° C. water bath for 30 minutes.

After staining, each 2-mm slice is photographed with a TMC-7 camera (JH Technologies, Calif.) and the image is captured and stored on a computer. This image is used for the measurements of the regions of interest using a computer-based image processing system (Metamorph).

To measure each area, the region of interest is selected using a freehand selection tool and the area is computed by selecting the measure command. The measurements for primary regions of interest are right hemisphere, left hemisphere, total infarct, subcortical infarct, total penumbra and subcortical penumbra. After all regions of interest are measured for all seven slices of the brain, they are sorted by slice number and the corresponding regions of interest using an Excell macro, Statistic Final. This macro also calculaes the cortical penumbra, cortical infarct and total ischemic damage for each slice then the corresponding areas of each rat brain are added together to produce a single measurement for each area. Since the ipsilateral hemisphere is swollen following MCAO, edema volume is calculated and reported as the volumetric differences between the right and left hemispheres of each brain slice. Using the percentage of hemispheric swelling, all the volumes are corrected for the edema.

The volume of the damage is determined using the calculations for each rat's brain as follows.

Cortical Penumbra: Total Penumbra−Subcortical Penumbra

Cortical Infarct: Total Infarct−Subcortical Infarct

Total Ischemic Damage: Total Penumbra+Total Infarct

Summary ($mm^2$): measurements of each column are added together.

Total Volume ($mm^3$): The sum of each column is multiplied by 2 (the thickness of the tissue).

Edema Volume: The volumetric differences between the sum of right and left hemispheres determine the edema volume.

% Hemispheric swelling (H.S.): Edema×100/left hemisphere

Correction for Edema for Each Measurement:

T.P. (Total Penumbra) corrected=T.P.−(T.P.×%H.S./100)
S.P. (Total Penumbra) corrected=S.P.−(S.P.×%H.S./100)
C.P. (Total Penumbra) corrected=C.P.−(C.P.×%H.S./100)
T.I. (Total infarct) corrected−T.I.=(T.I.×%H.S./100)
S.I. (Total infarct) corrected=S.I.=(S.I.×%H.S./100)
C.I. (Total infarct) corrected=CL=(C.I.×%H.S./100)
T.I.D. (Total Ischemic Damage) corrected=T.I.D.31 (T.I.D.×%H.S./100)

The sample size is chosen to achieve a 90% probability of significant results. The measurements, which represent the same region of interest in seven slices of each rat's brain are added together to yield a single measurement for total infarct, subcortical infarct, cortebral infarct, total penumbra, subcortical penumbra, cortical penumbra, total ischemic damage and edema in each animal. Group data are presented as means+/−SEM and $p<0.05$ are considered significant. A comparison of each region of interest between groups is carried out by unpaired student t test (between two groups) or one way ANOVA followed by post hoc Bonferroni's multiple comparisons or by the nonparametric Dunnett's test (between control and the drug treated groups).

2F. Results

When gamma-tocopherol enriched tocopherol composition (greater than 90% gamma-tocopherol) was administered I.V. at the time of MCAO, total infarct volume, total ischemic damage and cerebral edema were significantly reduced relative to that of control animals. Administration of the gamma-tocopherol metabolite, gamma-CEHC, I.V. at the time of MCAO also resulted in significantly reduced total infarct volume and total ischemic damage relative to that of controls. Administration of gamma-CEHC at the time of MCAO also resulted in reduced cerebral edema relative to that of control animals. Thus, administration of a gamma-tocopherol enriched tocopherol composition or a gamma-tocopherol metabolite enriched composition provided protection to the brain against damage and effects associated with cerebral ischemia.

Administration of a gamma-tocopherol enriched composition or a gamma-tocopherol metabolite enriched composition at the time of reperfusion resulted in reduction of total infarct volume, total ischemic damage and cerebral edema relative to that of controls.

The protective effects of alpha-tocopherol and delta-tocopherol were also assessed in the MCAO assay. At the same concentration, gamma-tocopherol was more effective in the reduction of total infarct volume and in the reduction of tissue edema than alpha- or delta-tocopherol. Delta-tocopherol was more effective in the reduction of total infarct volume than alpha-tocopherol.

Example 3

Animal Assay for Behavioral Recovery After Cerebral Ischemia

This assay is used to assess the efficacy of the test agents in behavioral recovery after cerebral ischemia induced in rats. Clinical behavior evaluation includes neurological examination, sensomotor activity and learning and memory behavior testing.

Three groups of animals, sham treated, MCAO animals treated with test agents and MCAO animals treated with control vehicle, are used. The time points of testing is dependent on the individual test.

Male Wistar rats are treated and MCAO is performed as described in Example 2A. Polyethylene catheters are inserted into a jaguar vein or femoral vein for blood sampling and drug administration.

After the animals regain consciousness, they are placed in the cooling system or refrigerator for cooling down the body temperature. The temperature in the cooling system or refrigerator is kept between 6 to 14° C. The animal body temperature is maintained at 37.5±1° C. during the operation and 24 hours post-ischemia reperfusion. Animal body temperature is recorded before the operation, during the operation and at 15, 30, 60, 90, 120, 180, 240 minutes and 24 hours post-operation.

The neurological status of each rat after MCAO is evaluated within 1, 4, 6, and 24 hour after induction of ischemia. Rats that extended both forelimbs toward the floor when held by the tail and that had no other neurological deficit are assigned a grade of zero. Rats with consistent forelimb flexion and which bent to the contralateral side when held by the tail, but no other abnormalities are graded 1. Rats that have consistently reduced resistance to lateral push and gait toward the paretic side are graded 2. Rats that circle toward the paretic side consistently within 1 hour after MCAO are graded 3. Animals which do not get grades of 2 or 3 are excluded from the study.

The test agents and controls are given by i.p. or i.v. bolus and/or continuous infusion as described in Example 2.

3A. Sensorimotor Behavior

Fore and Hindlimb Grip Strength Test in Rats

The animals (sham treated, MCAO animals treated with test agents and MCAO animals treated with control vehicle) are moved into the testing room 30 minutes before testing. A Computerized Grip Strength Meter for Rats (Dual stand Model, Columbus Instruments, USA) is used to measure grip strength. Prior to testing, each gauge is calibrated with a set of known weights and the apparatus adjusted for the size of animal (about ½ inch clearance on both side of the animal). The forelimb measurements are done with the meter in the tension peak mode to freeze the reading as the subject is pulled away from the grip bar. The hindlimb measurements are done with the meter in the compression peak mode to freeze the reading as the subject's hindlimbs are pulled over the bar toward the meter. The animal is hand-held by the investigator as it is pulled past the grip bars. The animal is held around the midsection, with the fingers and thumb curling under the body and the index finger on top, over the back and shoulders, with the tip of the finger by the animal's neck. Alternatively, the animals are grasped by the scruff of the neck with one hand and at the base of the tail with the other. Both methods of holding the animals leave the fore and hind limbs free to grasp the grip bars as the animal is moved past them. The animals are handled consistently. Typically, three successive readings are taken for each animal with an inter-trial interval long enough to record the data and zero both meters for the next trial.

Beginning on post-operative day 2, animals are given a test that assesses sensorimotor integration and testing is continued twice weekly until day 16 after MCAO operation. The studies are carried out in blinded-randomized fashion.

Treadmill Test in Rats

The animals (sham treated, MCAO animals treated with test agents and MCAO animals treated with control vehicle) are moved into the testing room 30 minutes before testing. A Rota-Rod Treadmill for Rats (7750 Accelerating Model from UGO BASILE, COMERIO-ITALY) is used to test ability to perform on a treadmill. Each rat has 2–3 training runs of 1–2 minutes at intervals of 2–3 hours before testing. The cylinder is set in motion before placing the rats in position. The rotor is started at a constant selected speed and the rats are placed, one by one, in their sections, at the'same time, the trip counter is reset to zero. The rats are placed on the treadmill in a manner that facilitates walking while minimizes struggling. Data acquisition from the treadmill occurs through the use of connections to BASILINK Cat. 2000 or to MINILINK Cat. 2500. The BASILINK is a modular self-sufficient Data Acquisition System that enables the gathering of a list in appropriate files and printing of experimental data generated by one or more instruments. The MINILINK is a compact, non-printing version of the Basilink, suitable for the processing of data generated by a limited number of instruments via a computer.

Beginning on post-operative day 2, animals are given this test and testing is continued twice weekly until day 16 after MCAO operation. The studies are carried out in blinded-randomized fashion.

3B. Evaluation of Ischemic Damage

Examination for brain tissue damage (infarct size) is performed as described in Example 2E.

We claim:

1. A method for treating and/or ameliorating a symptom of neuronal damage associated with a cerebral ischemic condition in a mammalian subject, comprising administering to the subject an effective amount of a non-alpha tocopherol enriched tocopherol composition, and by said administering, reducing neuronal damage related to said cerebral ischemic condition.

2. The method of claim 1 wherein the non-alpha tocopherol enriched tocopherol composition is a gamma-tocopherol enriched tocopherol composition.

3. The method of claim 1 wherein the non-alpha tocopherol enriched tocopherol composition is a beta-tocopherol enriched tocopherol composition.

4. The method of claim 1 wherein the non-alpha tocopherol enriched tocopherol composition is a delta-tocopherol enriched tocopherol composition.

5. The method of claim 1 wherein the cerebral ischemic condition is secondary to an occlusion of the cerebral vasculature.

6. The method of claim 5 wherein the occlusion is due to a thromboembolus.

7. The method of claim 1 wherein the cerebral ischemia is due to a spasm of the coronary vasculature.

8. The method of claim 1 wherein the cerebral ischemic condition is secondary to a cessation of cardiac function.

9. The method of claim 1 wherein the cerebral ischemic condition is secondary to a cardiopulmonary bypass procedure.

10. The method of claim 1 wherein the cerebral ischemic condition is secondary to a hemorrhagic event in the cerebral vasculature.

11. The method of claim 2 wherein said gamma-tocopherol enriched tocopherol composition comprises at least 60% gamma-tocopherol.

12. The method of claim 2 wherein said gamma-tocopherol enriched tocopherol composition comprises at least 65% gamma-tocopherol.

13. The method of claim 2 wherein said gamma-tocopherol enriched tocopherol composition comprises at least 70% ma-tocopherol.

14. The method of claim 2 wherein said gamma-tocopherol enriched tocopherol composition comprises at least 75% gamma-tocopherol.

15. The method of claim 2 wherein said gamma-tocopherol enriched tocopherol composition comprises at least 80% gamma-tocopherol.

16. The method of claim 2 wherein said gamma-tocopherol enriched tocopherol composition comprises at least 85% gamma-tocopherol.

17. The method of claim 2 wherein said gamma-tocopherol enriched tocopherol composition comprises at least 90% gamma-tocopherol.

18. The method of claim 2 wherein said gamma-tocopherol enriched tocopherol composition comprises at least 95% gamma-tocopherol.

19. The method of claim 2 wherein said gamma-tocopherol enriched tocopherol composition comprises at least 98% gamma-tocopherol.

20. The method of claim 3 herein said beta-tocopherol enriched tocopherol composition comprises at least 50% beta-tocopherol.

21. The method of claim 3 wherein said beta-tocopherol enriched tocopherol composition comprises at least 65% be-tocopherol.

22. The method of claim 3 wherein said beta-tocopherol enriched tocopherol composition comprises at least 75% beta-tocopherol.

23. The method of claim 3 wherein said beta-tocopherol enriched tocopherol composition comprises at least 90% beta-tocopherol.

24. The method of claim 3 wherein said beta-tocopherol enriched tocopherol composition comprises at least 95% beta-tocopherol.

25. The method of claim 3 wherein said beta-tocopherol enriched tocopherol composition comprises at least 98% beta-tocopherol.

26. The method of claim 4 wherein said delta-tocopherol enriched tocopherol composition comprises at least 50% delta-tocopherol.

27. The method of claim 4 wherein said delta-tocopherol enriched tocopherol composition comprises at least 65% delta-tocopherol.

28. The method of claim 4 wherein said delta-tocopherol enriched tocopherol composition comprises at least 75% delta-tocopherol.

29. The method of claim wherein said delta-tocopherol enriched tocopherol composition comprises at least 90%/o delta-tocopherol.

30. The method of claim 4 wherein said delta-tocopherol enriched tocopherol composition comprises at least 95% delta-tocopherol.

31. The method of claim 4 wherein said delta-tocopherol enriched tocopherol composition comprises at least 98% delta-tocopherol.

32. The method of claim 1 wherein said composition is a nutritional composition.

33. The method of claim 1 wherein said composition is a pharmaceutical composition.

34. The method of claim 1 wherein said composition is administered orally.

35. The method of claim 1 wherein said composition is administered parenterally.

36. The method of claim 1 wherein said composition comprises a non-alpha tocopherol in a range of 1–1000 mg per kg body weight of said mammalian subject.

37. The method of claim 1 wherein said composition comprises a non-alpha tocopherol in a range of 1–50 mg per kg body weight of said mammalian subject.

38. The method of claim 1 wherein said composition comprises a non-alpha tocopherol in a range of 10–100 mg per kg body weight of said mammalian subject.

39. The method of claim 1, wherein said neuronal damage is neuronal cell death.

40. The method of claim 1, wherein said neuronal damage is total cerebral infarct volume.

41. The method of claim 1, wherein said neuronal damage is total cerebral ischemic damage.

42. The method of claim 1, wherein said neuronal damage is cerebral tissue edema.

43. The method of claim 1, wherein said neuronal damage is cognitive dysfunction.

* * * * *